United States Patent
Maeda et al.

(10) Patent No.: US 12,129,521 B2
(45) Date of Patent: Oct. 29, 2024

(54) METHODS FOR DETECTION OF MACRO-HETEROPLASMY AND MICRO-HETEROPLASMY IN MITOCHONDRIAL DNA

(71) Applicant: Imel Biotherapeutics, Inc., Waltham, MA (US)

(72) Inventors: Ryotaro Maeda, Kyoto-fu (JP); Daisuke Kami, Kyoto-fu (JP); Satoshi Gojo, Kyoto-fu (JP)

(73) Assignee: Imel Biotherapeutics, Inc., Waltham, MA (US)

( * ) Notice: Subject to any disclaimer, the term of this patent is extended or adjusted under 35 U.S.C. 154(b) by 57 days.

(21) Appl. No.: 17/079,196

(22) Filed: Oct. 23, 2020

(65) Prior Publication Data

US 2021/0123104 A1     Apr. 29, 2021

Related U.S. Application Data

(60) Provisional application No. 62/925,677, filed on Oct. 24, 2019.

(51) Int. Cl.
C12Q 1/68          (2018.01)
C12P 19/34         (2006.01)
C12Q 1/6883        (2018.01)

(52) U.S. Cl.
CPC ...... *C12Q 1/6883* (2013.01); *C12Q 2600/112* (2013.01); *C12Q 2600/156* (2013.01)

(58) Field of Classification Search
CPC ............ C12Q 1/6883; C12Q 2600/156; C12Q 2600/112
See application file for complete search history.

(56) References Cited

U.S. PATENT DOCUMENTS

| | | |
|---|---|---|
| 8,039,587 B2 | 10/2011 | Khan |
| 8,058,065 B2 | 11/2011 | Yamanaka et al. |
| 8,278,104 B2 | 10/2012 | Yamanaka et al. |
| 10,370,458 B2 | 8/2019 | McCully et al. |
| 2011/0008310 A1 | 1/2011 | Cataldo et al. |
| 2011/0008778 A1 | 1/2011 | Seibel |
| 2011/0281269 A1 | 11/2011 | Deckman et al. |
| 2013/0034527 A1 | 2/2013 | Hyde et al. |
| 2013/0136726 A1 | 5/2013 | Sobenin et al. |
| 2018/0030413 A1 | 2/2018 | Yivgi-Ohana et al. |
| 2018/0057610 A1 | 3/2018 | McCully et al. |
| 2019/0024073 A1 | 1/2019 | Ekker et al. |
| 2019/0269731 A1 | 9/2019 | Han et al. |
| 2020/0009198 A1 | 1/2020 | Choi et al. |
| 2020/0054682 A1 | 2/2020 | Gojo et al. |
| 2021/0228642 A1 | 7/2021 | Yivgi-Ohana et al. |
| 2021/0275597 A1 | 9/2021 | Yivgi-Ohana et al. |

FOREIGN PATENT DOCUMENTS

| | | |
|---|---|---|
| CA | 2590552 | 11/2007 |
| WO | WO 2009/074337 | 6/2009 |
| WO | WO 2016/135723 | 9/2016 |
| WO | WO 2017/015567 | 1/2017 |
| WO | WO 2018/088874 | 5/2018 |
| WO | WO 2018/093954 | 5/2018 |
| WO | WO 2018/088875 | 8/2018 |
| WO | WO 2018/178970 | 10/2018 |
| WO | WO 2020/036973 | 2/2020 |

OTHER PUBLICATIONS

Selena Trifunov, et al., "Clonal expansion of mtDNA deletions: diferent disease models assessed by digital droplet PCR in single muscle cells" Nature—Scientific Reports vol. 8, Article No. 11682 (Published Aug. 3, 2018) (Year: 2018).*
Yoko Kobayahi, et al. "Single-Cell Analysis of Intercellular Heteroplasmy of mtDNA in Leber Hereditary Optic Neuropathy" Am.J. Hum. Genet. 55:206-209, 1994 (Year: 1994).*
Aird et al., "Analyzing and minimizing PCR amplification bias in Illumina sequencing libraries," Genome Biol. 12:18 (2011).
Albaryak et al., "The ability of human nuclear DNA to cause false positive low-abundance heteroplasmy calls varies across the mitochondrial genome," BMC Genom. 17:1017 (2016).
Alexeyev, "Is there more to aging than mitochondrial DNA and reactive oxygen species?," FEBS J., 276:5768-5787 (2009).
Amyere et al., "Origin, originality, functions, subversions and molecular singalling of micropinocytosis," Int. J. Med. Microbiol., 291:487-494 (2002).
Angulo et al., "A new generation of companion diagnostics: cobas BRAF, KRAS and EGFR mutation detection tests," Expert Rev. Mol. Diagn. 14, 517-524, (2014).
Aryaman et al., "Mitochondrial Heterogeneity," Front Genet 9, 718, doi:10.3389/fgene.2018.00718 (2018).
Aryaman et al., "Mitochondrial network fragmentation modulates mutant mtDNA accumulation independently of absolute fission-fusion rates," bioRxiv, 409128 (2018).
Attardi et al., "Complementation and segregation behavior of disease-causing mitochondrial DNA mutations in cellular model systems," Biochim. Biophys. Acta, 1271:241-248 (1995).
Bacman et al., "The use of mitochondria-targeted endonucleases to manipulate mtDNA," Methods in enzymology. vol. 547. Academic Press, 2014. 373-397 (2014).
Bacman et al., "Modulating mtDNA heteroplasmy by mitochondria-targeted restriction endonucleases in a 'differential multiple cleavage-site' model," Gene Ther., 14(18):1309-1318 (2007).
Bacman et al., "Organ-specific shifts in mtDNA heteroplasmy following systemic delivery of a mitochondria-targeted restriction endonuclease," Gene Ther., 17(6):713-720 (2010).

(Continued)

*Primary Examiner* — Stephen T Kapushoc
(74) *Attorney, Agent, or Firm* — COOLEY LLP

(57) ABSTRACT

The present disclosure provides methods for detecting macro-heteroplasmy and/or micro-heteroplasmy in mitochondrial DNA. The methods can include detecting or monitoring the presence of heteroplasmy, and/or identifying a threshold level of heteroplasmy. In addition, the methods can be used for diagnosing a mitochondrial related disease or disorder, as well as for monitoring the efficacy of a therapy affecting mitochondrial DNA (mtDNA) in a subject having or suspected of having heteroplasmy.

16 Claims, 23 Drawing Sheets

Specification includes a Sequence Listing.

(56) References Cited

OTHER PUBLICATIONS

Bacman et al., "Specific elimination of mutant mitochondrial genomes in patient- derived cells by mitoTALENs," Nat. Med., 19(9):1111-1113 (2013).
Bacman et al., "Transmitochondrial technology in animal cells," Methods Cell Biol., 80:503-524 (2007).
Bai et al., "Detection and quantification of heteroplasmic mutant mitochondrial DNA by real-time amplification refractory mutation system quantitative PCR analysis: a single-step approach,". Clin. Chem. 50:996-1001. https://doi.org/10.1373/ clinc hem.2004.03115 3 (2004).
Barritt et al., "Cytoplasmic transfer in assisted reproduction," Human Reproduction Update, 7(4):428-435 (2001).
Barritt et al., "Mitochondria in human offspring derived from ooplasmic transplantation," Hum. Reprod., 16(3):513-516 (2001).
Bates et al., "Cardiac involvement in mitochondrial DNA disease: clinical spectrum, diagnosis, and management," Eur. Heart J., 33(24):3023-3033 (2012).
Bayona-Bafaluy et al., "A chemical enucleation method for the transfer of mitochondrial DNA to p° cells," Nucl. Acids Res., 31(16):e98 (2003).
Bedwell et al., "Sequence and structural requirements of a mitochondrial protein import signal defined by saturation cassette mutagenesis," Mol. Cell. Biol., 9(3):1014-1025 (1989).
Bender et al., "High levels of mitochondrial DNA deletions in substantia nigra neurons in aging and Parkinson disease," Nat Genet 38, 515-517, doi:10.1038/ng1769 (2006).
Berridge et al., "Horizontal transfer of mitochondria between mammalian cells: beyond co-culture approaches," Curr. Opin. Genet. Dev., 38:75-82 (2016).
Berry et al., "Herpes Simplex Virus Type 1 Infection Disturbs the Mitochondrial Network, Leading to Type I Interferon Production through the RNA Polymerase III/RIG-I Pathway," Mbio 12.6 (2021): e02557-21.
Bertero et al., "Calcium Signaling and Reactive Oxygen Species in Mitochondria," Circ. Res., 122:1460-1478 (2018).
Birky et al., "An Approach to Population and Evolutionary Genetic Theory for Genes in Mitochondria and Chloroplasts, and Some Results," Genetics 103:513 (1983).
Birky Jr, "Relaxed and stringent genomes: why cytoplasmic genes don't obey Mendel's laws," Journal of Heredity 85, 355-365 (1994).
Blazej et al., "Polymorphism ratio sequencing: a new approach for single nucleotide polymorphism discovery and genotyping," Genome Res. 13:287-293. https ://doi.org/10.1101/gr.39620 3 (2003).
Bodnar et al., "Extension of life-span by introduction of telomerase into normal human cells," Science, 279:349-352 (1998).
Brandon et al., "MITOMAP: a human mitochondrial genome database—2004 update," Nucleic Acids Res. 33:D611-613. https://doi.org/10.1093/nar/gki07 9 (2005).
Bredenoord et al., "Mitochondrial Replacement Techniques: Remaining Ethical Challenges," Cell Stem Cell, 21(3):301-304 (2017).
Brehme et al., "A chaperome subnetwork safeguards proteostasis in aging and neurodegenerative disease," Cell Reports, 9:1135-1150 (2014).
Brown et al., "Rapid evolution of animal mitochondrial DNA," Proceedings of the National Academy of Sciences 76.4 (1979): 1967-1971.
Burke et al., "Mitochondria, Bioenergetics and Apoptosis in Cancer," Trends Cancer, 3(12):857-870 (2017).
Burrows et al., "Rapid and transient inhibition of mitochondrial function following methamphetamine or 3,4-methylenedioxymethamphetamine administration," Eur. J. Pharmacol., 398:11-18 (2000).
Caicedo et al., "Artificial Mitochondria Transfer: Current Challenges, Advances, and Future Applications," Stem Cells Int., 2017:7610414 (2017).
Calabrese et al., "Primates and mouse NumtS in the UCSC genome browser," BMC Bioinform. 13:S15 (2012).
Cantuti-Castlevestri et al., "Somatic mitochondrial DNA mutations in single neurons and glia," Neurobiol. Aging 26:1343-1355 (2005).

Chang et al., "Treatment of human cells derived from MERRF syndrome by peptide-mediated mitochondrial delivery," Cytotherapy 15(12):1580-1596 (2013).
Chen et al., "BEAMing and droplet digital PCR analysis of mutant IDH1 mRNA in glioma patient serum and cerebrospinal fluid extracellular vesicles," Mol. Ther. Nucleic Acids 2:109. https ://doi.org/10.1038/mtna.2013.28 (2013).
Cherry et al., "Induced pluripotent stem cells with a mitochondrial DNA deletion," Stem Cells, 31:1287-1297 (2013).
Chinnery et al., "Mitochondrial disease in adults: what's old and what's new?," EMBO Mol. Med., 7(12):1503-1512 (2015).
Chinnery et al., "Molecular pathology of MELAS and MERRF. The relationship between mutation load and clinical phenotypes," Brain, 120(Pt 10):1713-1721 (1997).
Chinnery et al., "Relaxed replication of mtDNA: a model with implications for the expression of disease,". The American Journal of Human Genetics 64:1158-1165 (1999).
Chomyn et al. "Platelet-mediated transformation of mtDNA-less human cells: analysis of phenotypic variability among clones from normal individuals—and complementation behavior of the tRNALys mutation causing myoclonic epilepsy and ragged red fibers." American journal of human genetics 54.6 (1994): 966.
Chondrogianni et al., "Proteasome activation: an innovative promising approach for delaying aging and retarding age-related diseases," Ageing Res. Rev., 23:37-55 (2015).
Chou et al., "Impaired ROS Scavenging System in Human Induced Pluripotent Stem Cells Generated from Patients with MERRF Syndrome," Sci. Rep., 6:23661 (2016).
Clark et al., "Selfish little circles: transmission bias and evolution of large deletion-bearing mitochondrial DNA in Caenorhabditis briggsae nematodes," PLoS One 7:41433, doi:10.1371/journal.pone.0041433 (2012).
Coppé et al., "Senescence-associated secretory phenotypes reveal cell-nonautonomous functions of oncogenic RAS and the p53 tumor suppressor," PLoS Biol., 6(12):2853-2868 (2008).
Correia-Melo et al., "Mitochondria are required for pro-ageing features of the senescent phenotype," EMBO J., 35(7):724-742 (2016).
Cree et al., "A reduction of mitochondrial DNA molecules during embryogenesis explains the rapid segregation of genotypes," Nat Genet 40, 249-254, doi:10.1038/ng.2007.63 (2008).
D'Souza et al., "Mitochondrial leader sequence-plasmid DNA conjugates delivered into mammalian cells by DQAsomes co-localize with mitochondria." *Mitochondrion* 5.5 (2005): 352-358.
Dong et al., "Horizontal transfer of whole mitochondria restores tumorigenic potential in mitochondrial DNA-deficient cancer cells," Elife, 6:e22187 (2017).
Dotti et al., "Design and Development of Therapies using Chimeric Antigen Receptor-Expressing T cells," Immunol Rev., 257(1):1-35, doi:10.1111/imr.12131 (2014).
Duan et al., "Evaluating heteroplasmic variations of the mitochondrial genome from whole genome sequencing data". Gene 699, 145-154. https://doi.org/10.1016/j.gene.2019.03.016 (2019).
Duguay et al., "Elimination of mitochondrial DNA is not required for herpes simplex virus 1 replication," Journal of Virology 88.5 (2014): 2967-2976.
Duguay et al., "Mitochondrial nucleases ENDOG and EXOG participate in mitochondrial DNA depletion initiated by herpes simplex virus 1 UL12. 5," Journal of virology 87.21 (2013): 11787-11797.
Dunham-Snary et al., "Mitochondrial-nuclear DNA mismatch matters," Science, 349:1449-1450 (2015).
Durham et al., "Progressive depletion of mtDNA in mitochondrial myopathy," Neurology 67, 502-504 (2006).
El-Hattab et al., "Mitochondrial DNA maintenance defects". Biochim Biophys Acta Mol Basis Dis 1863, 1539-1555, doi:10.1016/j.bbadis.2017.02.017 (2017).
Facucho-Oliveira et al., "Mitochondrial DNA replication during differentiation of murine embryonic stem cells," J. Cell Sci., 120(Pt 22):4025-4034 (2007).
Fiorese et al., "The Transcription Factor ATF5 Mediates a Mammalian Mitochondrial UPR," Curr. Biol., 26:2037-2043 (2016).

(56) References Cited

OTHER PUBLICATIONS

Fisicaro et al., "Targeting mitochondrial dysfunction can restore antiviral activity of exhausted HBV-specific CD8 T cells in chronic hepatitis B," Nat Med., 23(3):1-10 doi:10.1038/nm.4275 (2017).
Fliedl et al., "Optimization of a quantitative PCR based method for plasmid copy number determination in human cell lines," New Biotechnol., 32(6):716-719 (2015).
Folmes et al., "Disease-causing mitochondrial heteroplasmy segregated within induced pluripotent stem cell clones derived from a patient with MELAS," Stem Cells, 31:1298-1308 (2013).
Frezza et al., "Organelle isolation: functional mitochondria from mouse liver, muscle and cultured filroblasts," Nature Protocol, 2(2):287-295 (2007).
Fujikura et al., "Induced pluripotent stem cells generated from diabetic patients with mitochondrial DNA A3243G mutation," Diabetologia, 55:1689-1698 (2012).
Galera et al., "Generation of a human iPSC line from a patient with Leigh syndrome," Stem Cell Res., 16:63-66 (2016).
Gasnier et al., "Use of Percoll Gradients for Isolation of Human Placenta Mitochondria Suitable for Investigating Outer Membrane Proteins," Analytical Biochemistry, 212:173-178 (1993).
Ghosh et al., "Use of cytoplasmic hybrid cell lines for elucidating the role of mitochondrial dysfunction in Alzheimer's disease and Parkinson's disease," Ann. N.Y. Acad. Sci., 893:176-191 (1999).
Gibson, N. J. "The use of real-time PCR methods in DNA sequence variation analysis," Clin Chim Acta 363, 32-47, doi:10.1016/j.cccn. 2005.06.022 (2006).
Gollihue et al., "Prospects for therapeutic mitochondrial transplantation," Mitochondrian 35:70-79 (2017).
Gollihue et al., "Mitochondrial transplantation strategies as potential therapeutics for central nervous system trauma," Neural Regen. Res., 13(2):194-197 (2018).
Gomes et al., "Declining NAD+ induces a pseudohypoxic state disrupting nuclear-mitochondrial communication during aging," Cell, 155:1624-1638 (2013).
Gonzalez et al., "Nutrient sensing and TOR signaling in yeast and mammals," EMBO J., 36:397-408 (2017).
Gorman et al., "Mitochondrial diseases," Nat Rev Dis Primers 2, 16080, doi:10.1038/nrdp.2016.80 (2016).
Greenfield et al., "Assisted reproductive technologies to prevent human mitochondrial disease transmission," Nat. Biotechnol., 35:1059-1068 (2017).
Guedan et al., "Engineering and Design of Chimeric Antigen Receptors," Mol. Ther. Methods Clin. Dev., 12:145-156 (2018).
Hamalainen et al., "Tissue- and cell-type-specific manifestations of heteroplasmic mtDNA 3243A>G mutation in human induced pluripotent stem cell-derived disease model," Proc. Natl. Acad. Sci. USA, 110:E3622-E3630 (2013).
Harley et al., "Telomeres shorten during ageing of human fibroblasts," Nature, 345:458-460 (1990).
Hartwig et al., "A critical comparison between two classical and a kit-based method for mitochondria isolation," Proteomics, 9(11):3209-3214 (2009).
Harvey et al., "Characterization and applications of CataCleave probe in real-time detection assays," Anal Biochem 333, 246-255, doi:10.1016/j.ab.2004.05.037 (2004).
Hashimoto et al., "MitoTALEN: A General Approach to Reduce Mutant mtDNA Loads and Restore Oxidative Phosphorylation Function in Mitochondrial Diseases," Mol. Ther., 23: 1592-1599 (2015).
Hatakeyama et al., "Concise Review: Heteroplasmic Mitochondrial DNA Mutations and Mitochondrial Diseases: Toward iPSC-Based Disease Modeling, Drug Discovery, and Regenerative Therapeutics," Stem Cells, 34(4):801-808 (2016).
Hayakawa et al., "Transfer of mitochondria from astrocytes to neurons after stroke," Nature, 535:551-555 (2016).
Hayflick, "The limited in vitro lifetime of human diploid cell strains," Experimental Cell Res., 37:614-636 (1965).

He et al., "Heteroplasmic mitochondrial DNA mutations in normal and tumour cells," Nature 464, 610-614; https://doi.org/10.1038/nature 08 802 (2010).
Heller et al., "Efficient repopulation of genetically derived rho zero cells with exogenous mitochondria," PLoS One, 8(9):e73207 (2013).
Holland et al., "Detection of specific polymerase chain reaction product by utilizing the 5' -> 3' exonuclease activity of Thermus aquaticus DNA polymerase," Proceedings of the National Academy of Sciences 88, 7276, doi:10.1073/pnas.88.16.7276 (1991).
Holt et al., "Deletions of muscle mitochondrial DNA in patients with mitochondrial myopathies," Nature 331, 717-719, doi:10.1038/331717a0 (1988).
Hsu et al., "Mitochondrial resetting and metabolic reprogramming in induced pluripotent stem cells and mitochondrial disease modeling," Biochim. Biophys. Acta, 1860:686-693 (2016).
Huang et al., "Extension of base mispairs by Taq DNA polymerase: implications for single nucleotide discrimination in PCR," Nucleic Acids Research 20, 4567-4573, doi:10.1093/nar/20.17.4567 (1992).
Huang et al., "Kissing and nanotunneling mediate intermitochondrial communication in the heart," Proc. Natl. Acad. Sci. U.S.A., 110(8):2846-2851 (2013).
Huang et al., "Multiplex fluorescence melting curve analysis for mutation detection with dual-labeled, self-quenched probes," PLoS One 6, e19206, doi:10.1371/journal.pone.0019206 (2011).
Huggett et al., "The Digital MIQE Guidelines: Minimum Information for Publication of Quantitative Digital PCR Experiments," Clinical Chemistry 59, 892, doi:10.1373/clinchem.2013.206375 (2013).
Igarashi et al., "Single cell-based vector tracing in patients with ADA-SCID treated with stem cell gene therapy," Mol. Ther. Methods Clin. Dev. 6, 8-16 (2017).
International Search Report and Written Opinion issued on PCT/US2020/057165, dated Jan. 21, 2021 (11 pages).
Islam et al., "Mitochondrial transfer from bone-marrow-derived stromal cells to pulmonary alveoli protects against acute lung injury," Nat. Med., 18(5):759-765 (2012).
Jackaman et al., "CD8+ cytotoxic T cell responses to dominant tumor-associated antigens are profoundly weakened by aging yet subdominant responses retain functionality and expand in response to chemotherapy," OncoImmunology, 8(4):e1564452 (2019).
Jayaprakash et al., "Stable heteroplasmy at the single-cell level is facilitated by intercellular exchange of mtDNA," Nucleic Acids Res. 43, 2177-2187. https://doi.org/10.1093/nar/gkv05 2 (2015).
Ji et al., "Enucleation of cultured mouse fetal erythroblasts requires Rac GTPases and mDia2," Nat. Cell Biol., 10(3):314-321 (2008).
Jo et al., "Efficient Mitochondrial Genome Editing by CRISPR/Cas9," BioMed Res. Int., 2015:1-10 (2015).
Johne et al., "Rolling-circle amplification of viral DNA genomes using phi29 polymerase," Trends Microbiol. 17, 205-211. https://doi.org/10.1016/j.tim.2009.02.004 (2009).
Jorgensen et al., "Companion and complementary diagnostics: clinical and regulatory perspectives," Trends in cancer 2, 706-712 (2016).
Kagawa et al., "Gene therapy of mitochondrial diseases using human cytoplasts," Gene Ther., 4:6-10 (1997).
Kang et al., "Age-Related Accumulation of Somatic Mitochondrial DNA Mutations in Adult-Derived Human iPSC," Cell Stem Cell, 18(5):625-636 (2016).
Kang et al., "The DNA damage response induces inflammation and senescence by inhibiting autophagy of GATA4," Science, 349(6255):aaa5612-1-aaa5612-11 (2015).
Kauppila et al., "Mammalian Mitochondria and Aging: An Update," Cell Metabolism, 25:57-71 (2017).
Kauppila et al., "Mitochondrial DNA: Radically free of free-radical driven mutations," Biochim Biophys Acta 1847, 1354-1361, doi:10.1016/j.bbabio.2015.06.001 (2015).
Kesner et al., "Characteristics of Mitochondrial Transformation into Human Cells," Sci. Rep., 6:26057 (2016).
Khan et al., "Development of mitochondrial gene replacement therapy." Journal of bioenergetics and biomembranes 36.4 (2004): 387-393.
Kim et al., "Delivery of exogenous mitochondria via centrifugation enhances cellular metabolic function," Sci. Rep., 8(1):3330 (2018).

(56) References Cited

OTHER PUBLICATIONS

King et al., "Human cells lacking mtDNA: repopulation with exogenous mitochondria by complementation," Science, 246:500-503 (1989).
King et al., "Injection of mitochondria into human cells," Cell, 52(6):811-819 (1988).
Kitani et al., "Direct human mitochondrial transfer: a novel concept based on the endosymbiotic theory," Transplant Proc., 46(4):1233-1236 (2014).
Kitani et al., "Internalization of isolated functional mitochondria: involvement of micropinocytosis," J. Cell Mol. Med., 18(8):1694-1703 (2014).
Kodaira et al., "Impaired respiratory function in MELAS-induced pluripotent stem cells with high heteroplasmy levels," FEBS Open Bio., 5:219-225 (2015).
Kraytsberg et al., "Recombination of human mitochondrial DNA," Science, 304:981 (2004).
Kuilman et al., "Senescence-messaging secretome: SMS-ing cellular stress," Nature Rev. Cancer, 9:81-94 (2009).
Kukat et al., "Generation of rho0 cells utilizing a mitochondrially targeted restriction endonuclease and comparative analyses," Nucleic Acids Res., 36(7):e44 (2008).
Kunkel et al., "Mitochondrial pathways to cardiac recovery: TFAM," Heart Fail Rev., 21(5):499-517 (2016).
Kyriakouli et al., "Progress and prospects: gene therapy for mitochondrial DNA disease," Gene Ther., 15(14):1017-1023 (2008).
Labbadia et al., "The biology of proteostasis in aging and disease," Ann. Rev. Biochem., 84:435-464 (2015).
Lane et al., "The energetics of genome complexity," Nature 467, 929-934, doi:10.1038/nature09486 (2010).
Lang et al., "Purification of mitochondrial and plastid DNA". Nat Protoc. 2, 652-660; https://doi.org/10.1038/nprot2007.58 (2007).
Lapasset et al., "Rejuvenating senescent and centenarian human cells by reprogramming through the pluripotent state," Genes Dev., 25:2248-2253 (2011).
Le Saux et al., "Mechanisms of immunosenescence: lessons from models of accelerated immune aging," Ann N Y Acad Sci., 1247:69-82 (2012).
Leng et al., "Agarose Droplet Microfluidics for Highly Parallel and Efficient Single Molecule Emulsion PCR," Lab Chip 10, 2841-2843. https://doi.org/10.1039/C0LC0 0145G (2010). emulsion PCR. Lab Chip 10, 2841-2843. https://doi.org/10.1039/C0LC0 0145G (2010).
Li et al., "Droplet digital PCR shows the D-loop to be an error prone locus for mitochondrial DNA copy number determination," Sci. Rep. 8, 11392. https://doi.org/10.1038/s41598-018-29621-1 (2018).
Liang et al., "Generation of MERRF patient-derived induced pluripotent stem cell line iMERRF-C7," Stem Cell Res., 17:616-618 (2016).
Lightowlers et al., "Mutations causing mitochondrial disease: What is new and what challenges remain?," Science, 349(6255):1494-1499 (2015).
Lin et al., "Maintenance and propagation of a deleterious mitochondrial genome by the mitochondrial unfolded protein response," Nature, 533(7603):416-419 (2016).
Linnane et al., "Mitochondrial DNA mutations as an important contributor to ageing and degenerative diseases," Lancet 333:642-645 (1989).
Lis et al., "Conversion of adult endothelium to immunocompetent haematopoietic stem cells," Nature, 545:439-445 (2017).
Liu et al., "DNA repair in mammalian mitochondria: Much more than we thought?," Environ. Mol. Mutagen., 51:417-426 (2010).
Liu et al., "Mitochondrial 'kiss-and-run': interplay between mitochondrial motility and fusion-fission dynamics," EMBO J., 28(20):3074-3089 (2009).
Lopez-Otin et al., "The hallmarks of aging," Cell, 153:1194-1217 (2013).
Ma et al., "Metabolic rescue in pluripotent cells from patients with mtDNA disease," Nature, 524(7564):234-238 (2015).

Machado et al., "Real-time PCR quantification of heteroplasmy in a mouse model with mitochondrial DNA of C57BL/6 and NZB/BINJ strains," PLoS One 10, e0133650. https://doi.org/10.1371/journal.pone.0133650 (2015).
Madeo et al., "Essential role for autophagy in life span extension," J. Clin. Invest., 125(1):85-93 (2015).
Maeda et al., "Generation of somatic mitochondrial DNA-replaced cells for mitochondrial dysfunction treatment," Scientific Reports 11(1):1-16 (2021).
Maricic et al., "Multiplexed DNA sequence capture of mitochondrial genomes using PCR products," PLoS One 5, e14004. https://doi.org/10.1371/journal.pone.00140 04 (2010).
Marquis et al., "MitoRS, a method for high throughput, sensitive, and accurate detection of mitochondrial DNA Heteroplasmy," BMC Genom. 18, 326. https://doi.org/10.1186/s1286 4-017-3695-5 (2017).
Mazaika et al., "Digital Droplet PCR: CNV Analysis and Other Applications," Curr Protoc Hum Genet 82, 7.24.1-7.24.13 (2014).
McKernan et al., "Expanded genetic codes in next generation sequencing enable decontamination and mitochondrial enrichment," PLoS One 9, e96492. https://doi.org/10.1371/journ al.pone.00964 92 (2014).
Melber et al., "UPR(mt) regulation and output: a stress response mediated by mitochondrial-nuclear communication," Cell Res., 28:281-295 (2018).
Mercer et al., "Virus entry by macropinocytosis," Nature Cell Biol., 11(5):510-520 (2009).
Mills et al., "Mitochondria are the powerhouses of immunity," Nat. Immunol., 18(5):488-498 (2017).
Morris et al., "Pervasive within-Mitochondrion Single-Nucleotide Variant Heteroplasmy as Revealed by Single-Mitochondrion Sequencing," Cell Rep 21, 2706-2713, doi:10.1016/j.celrep.2017.11.031 (2017).
Moschoi et al., "Protective mitochondrial transfer from bone marrow stromal cells to acute myeloid leukemic cells during chemotherapy," Blood, 128(2):253-264 (2016).
Nacarelli et al., "Inhibition of mTOR prevents ROS production initiated by ethidium bromide-induced mitochondrial DNA depletion," Frontiers in endocrinology 5 (2014): 122.
Nargund et al., "Mitochondrial and nuclear accumulation of the transcription factor ATFS-1 promotes OXPHOS recovery during the UPR(mt)," Mol. Cell, 58:123-133 (2015).
Newton et al., "Analysis of any point mutation in DNA. The amplification refractory mutation system (ARMS)," Nucleic Acids Research 17, 2503-2516, doi:10.1093/nar/17.7.2503 (1989).
Niazi et al., "Targeting nucleic acids into mitochondria: progress and prospects," Mitochondrion., 13:548-558 (2013).
Nunnari et al., "A. Mitochondria: in sickness and in health," Cell, 148:1145-1159 (2012).
Nurmi et al., "A new label technology for the detection of specific polymerase chain reaction products in a closed tube," Nucleic acids research 28, e28-00 (2000).
O'Hara et al., "Quantitative mitochondrial DNA copy number determination using droplet digital PCR with single cell resolution," Genome Res. https://doi.org/10.1101/gr.250480.119 (2019).
Osborne et al., "Single-molecule LATE-PCR analysis of human mitochondrial genomic sequence variations," PLoS One 4(5):e5636 (2009).
Ouwehand, W. H., "Whole-genome sequencing of rare disease patients in a national healthcare system," bioRxiv, 507244 (2020).
Pace et al., "Repeated horizontal transfer of a DNA transposon in mammals and other tetrapods," Proc. Natl.Acad. Sci. USA, 105(44):17023-17028 (2008).
Palm et al., "The Utilization of Extracellular Proteins as Nutrients Is Suppressed by mTORC1," Cell, 162(2):259-270 (2015).
Patel et al., "Macropinocytic entry of isolated mitochondria in epidermal growth factor-activated human osteosarcoma cells," Sci. Rep., 7(1):12886 (2017).
Payungporn et al., "Simultaneous quantitation and genotyping of hepatitis B virus by real-time PCR and melting curve analysis," J Virol Methods 120, 131-140, doi:10.1016/j.jviromet.2004.04.012 (2004).

(56) References Cited

OTHER PUBLICATIONS

Perry et al., "Mitochondrial membrane potential probes and the proton gradient: a practical usage guide," Biotechniques, 50(2):98-115 (2011).
Preble et al., "Rapid Isolation and Purification of Mitochondria for Transplantation by Tissue Dissociation and Differential Filtration," J. Vis. Exp., (91):e51682, doi:10.3791/51682 (2014).
Pye et al., "Production of transmitochondrial cybrids containing naturally occurring pathogenic mtDNA variants," Nucleic Acids Res., 34(13):e95 (2006).
Quinn et al., "Age-Related Decline in Primary CD8+ T Cell Responses is Associated with the Development of Senescence in Virtual Memory CD8+ T Cells," Cell Reports, 23:3512-3524 (2018).
Quiros et al., "Mitonuclear communication in homeostasis and stress," Nat. Rev. Mol. Cell. Biol., 17:213-226 (2016).
Rajasimha et al., "Selection against pathogenic mtDNA mutations in a stem cell population leads to the loss of the 3243A-->G mutation in blood," Am J Hum Genet 82, 333-343, doi:10.1016/j.ajhg.2007.10.007 (2008).
Rampelt et al., "Coordination of Two Genomes by Mitochondrial Translational Plasticity," Cell, 167:308-310 (2016).
Raval et al., "Cardiomyopathy, mitochondria and Barth syndrome: iPSCs reveal a connection," Nat. Med., 20:585-586 (2014).
Rocca et al., "Transplantation of wild-type mouse hematopoietic stem and progenitor cells ameliorates deficits in a mouse model of Friedreich's ataxia," Sci. Transl. Med., 9(413): doi:10.1126/scitranslmed.aaj2347 (2017).
Rossignol et al., "Mitochondrial threshold effects," The Biochemical Journal 370, 751-762, doi:10.1042/BJ20021594 (2003).
Rustom et al., "Nanotubular highways for intercellular organelle transport," Science, 303:1007-1010 (2004).
Saeidi et al., "T-Cell Exhaustion in Chronic Infections: Reversing the State of Exhaustion and Reinvigorating Optimal Protective Immune Responses," Frontier Immunol., 9(2569):1-12 doi: 10.3389/fimmu.2018.02569 (2018).
Saffran et al., "Herpes simplex virus eliminates host mitochondrial DNA," EMBO reports 8.2 (2007): 188-193.
Sahin et al., "Axis of ageing: telomeres, p53 and mitochondria," Nat. Rev. Mol. Cell Biol., 13(6):397-404 (2012).
Sahin et al., "Telomere dysfunction induces metabolic and mitochondrial compromise," Nature, 470(7334):359-365 (2011).
Santibanez-Koref et al., "Assessing mitochondrial heteroplasmy using next generation sequencing: a note of caution," Mitochondrion 46, 302-306. https://doi.org/10.1016/j.mito.2018.08.003 (2019).
Schmitt et al., "Detection of ultra-rare mutations by next-generation sequencing," Proc. Natl. Acad. Sci. U. S. A. 109, 14508-14513. https://doi.org/10.1073/pnas.12087 15109 (2012).
Sebastian et al., "Mitochondrial Dynamics: Coupling Mitochondrial Fitness with Healthy Aging," Trends Mol Med 23, 201-215, doi:10.1016/j.molmed.2017.01.003 (2017).
Smeitink et al., "Mitochondrial medicine: a metabolic perspective on the pathology of oxidative phosphorylation disorders," Cell Metab., 3:9-13 (2006).
Smith et al., "Altering the balance between healthy and mutated mitochondrial DNA," J. Inherited Metabol. Dis., 34:309-313 (2011).
Spees et al., "Mitochondrial transfer between cells can rescue aerobic respiration," Proceedings of the National Academy of Sciences 103(5):1283-1288 (2006).
Stewart et al., "The dynamics of mitochondrial DNA heteroplasmy: implications for human health and disease," Nat Rev Genet 16, 530-542, doi:10.1038/nrg3966 (2015).
Sugimura et al., "Haematopoietic stem and progenitor cells from human pluripotent stem cells," Nature, 545:432-438 (2017).
Suhr et al. "Mitochondrial rejuvenation after induced pluripotency," PLoS One, 5(11):e14095 (2010).
Sun et al., "New strategy for in vitro activation of primordial follicles with mTOR and PI3K stimulators," Cell Cycle, 14(5):721-731 (2015).
Sun et al., "The Mitochondrial Basis of Aging," Mol. Cell, 61(5):654-666 (2016).
Sung et al., "Catabolic pathways regulated by mTORC1 are pivotal for survival and growth of cancer cells expressing mutant Ras," Oncotarget, 6:40405-40417 (2015).
Suomalainen et al., "FGF-21 as a biomarker for muscle-manifesting mitochondrial respiratory chain deficiencies: a diagnostic study," The Lancet Neurology 10, 806-818, doi:10.1016/s1474-4422(11)70155-7 (2011).
Suomalainen et al., "Mitochondrial diseases: the contribution of organelle stress responses to pathology," Nat. Rev. Mol. Cell Biol., 19:77-92 (2018).
Tachibana et al., "Human Embryonic Stem Cells Derived by Somatic Cell Nuclear Transfer," Cell, 153:1228-1238 (2013).
Tachibana et al., "Mitochondrial gene replacement in primate offspring and embryonic stem cells," Nature, 461:367-372 (2009).
Takahashi et al., "Induction of pluripotent stem cells from mouse embryonic and adult fibroblast cultures by defined factors," Cell 126:663-676 (2006).
Takahashi et al., "Induction of pluripotent stem cells from adult human fibroblasts by defined factors," Cell, 131(5):861-872 (2007).
Tan et al., "Mitochondrial genome acquisition restores respiratory function and tumorigenic potential of cancer cells without mitochondrial DNA," Cell Metab., 21:81-94 (2015).
Tanaka et al., "Gene therapy for mitochondrial disease by delivering restriction endonuclease SmaI into mitochondria," J. Biomed. Sci., 9:534-541 (2002).
Tatuch et al., "Heteroplasmic mtDNA mutation (T—G) at 8993 can cause Leigh disease when the percentage of abnormal mtDNA is high," American journal of human genetics 50, 852-858 (1992).
Tian et al., "Mitochondrial UPR: A Double-Edged Sword," Trends Cell Biol., 26:563-565 (2016).
Torralba et al., "Mitochondria know No. boundaries: mechanisms and functions of intercellular mitochondrial transfer," Frontiers in cell and developmental biology 4 (2016): 107.
Transient Transfection. Thermo Fisher Scientific. downloaded from web.archive.org/web/20150912051020/https://www.thermofisher.com/us/en/home/references/gibco-cell-culture-basics/transfection-basics/transfection-methods/transient-transfection.html. p. 1-2 (2015).
Tuppen et al., "Mitochondrial DNA mutations and human disease," Biochimica et Biophysica Acta, 1797(2):113-128 (2010).
Turro, E.,. et al. "Whole-genome sequencing of patients with rare diseases in a national health system." Nature 583, 96-102 (2020).
Twig et al., "Fission and selective fusion govern mitochondrial segregation and elimination by autophagy," The EMBO Journal 27, 433-446, doi:10.1038/sj.emboj.7601963 (2008).
Urata et al., "High-sensitivity detection of the A3243G mutation of mitochondrial DNA by a combination of allele-specific PCR and peptide nucleic acid-directed PCR clamping," Clin Chem 50, 2045-2051, doi:10.1373/clinchem.2004.033761 (2004).
Vilchez et al., "The role of protein clearance mechanisms in organismal ageing and age-related diseases," Nat. Comm., 5:5659 (2014).
Wahlestedt et al., "Somatic Cells with a Heavy Mitochondrial DNA Mutational Load Render Induced Pluripotent Stem Cells with Distinct Differentiation Defects," Stem Cells, 32:1173-1182 (2014).
Wai et al., "The mitochondrial DNA genetic bottleneck results from replication of a subpopulation of genomes," Nature Genetics 40, 1484-1488, doi:10.1038/ng.258 (2008).
Wang et al., "Modeling the mitochondrial cardiomyopathy of Barth syndrome with induced pluripotent stem cell and heart-on-chip technologies," Nat. Med., 20(6):616-623 (2014).
Watanabe et al., "Ultra-Sensitive Detection of the Pretreatment EGFR T790M Mutation in Non-Small Cell Lung Cancer Patients with an EGFR-Activating Mutation Using Droplet Digital PCR," Clinical Cancer Research 21, 3552, doi:10.1158/1078-0432.CCR-14-2151 (2015).
Wei et al., "Selective removal of mitochondria via mitophagy: distinct pathways for different mitochondrial stresses," Biochim Biophys Acta 1853, 2784-2790, doi:10.1016/j.bbamcr.2015.03.013 (2015).
Weinberg et al., "Mitochondrial complex III is essential for regulatory T cell suppressive function," Nature, 565(7740):495-499, doi:10.1038/s41586-018-0846-z (2019).

(56) References Cited

OTHER PUBLICATIONS

Wherry, "T cell exhaustion," Nature immunology, 12(6):492-499 (2011).
Whitcombe et al., "Detection of PCR products using self-probing amplicons and fluorescence," Nature Biotechnology 17, 804-807, doi:10.1038/11751 (1999).
Wilkinson et al., "Long-term ex vivo haematopoietic-stem-cell expansion allows nonconditioned transplantation," Nature, 571(7763):117-121 (2019).
Wonnapinij et al., "The distribution of mitochondrial DNA heteroplasmy due to random genetic drift," Am J Hum Genet 83, 582-593, doi:10.1016/j.ajhg.2008.10.007 (2008).
Wu et al., "Generation of an induced pluripotent stem cell (iPSC) line from a 40-year-old patient with the A8344G mutation of mitochondrial DNA and MERRF (myoclonic epilepsy with ragged red fibers) syndrome," Stem Cell Res., 27:10-14 (2018).
Wu et al., "Mitochondrial Transfer by Photothermal Nanoblade Restores Metabolite Profile in Mammalian Cells," Cell Metab., 23:921-929 (2016).
Xu et al., "Manipulating the metazoan mitochondrial genome with targeted restriction enzymes," Science, 321(5888):575-577 (2008).
Yatsuga et al., "Growth differentiation factor 15 as a useful biomarker for mitochondrial disorders," Ann Neurol 78, 814-823, doi:10.1002/ana.24506 (2015).
Ye et al., "T-cell exhaustion in chronic hepatitis B infection: current knowledge and clinical significance," Cell Death and Disease, 6:e1694, doi:10.1038/cddis.2015.42 (2015).
Yokota et al., "Mitochondrial respiratory dysfunction caused by a heteroplasmic mitochondrial DNA mutation blocks cellular reprogramming," Hum. Mol. Genet., 24(16):4698-4709 (2015).
Zeviani et al., "Mitochondrial disorders," Brain, 127(Pt 10):2153-2172 (2004).
Zhang et al., "Fructose-1,6-bisphosphate and aldolase mediate glucose sensing by AMPK," Nature, 548(7665):112-116 (2017).
Zhang et al., "Pregnancy derived from human zygote pronuclear transfer in a patient who had arrested embryos after IVF," Reprod. Biomed. Online, 33(4):529-533 (2016).
Zhang et al., "Ultrasensitive and quantitative detection of EGFR mutations in plasma samples from patients with non-small-cell lung cancer using a dual PNA clamping-mediated LNA-PNA PCR clamp," Analyst 144, 1718-1724 (2019).
Corcoran et al., 2009, "Herpes Simplex Virus UL12.5 Targets Mitochondria through a Mitochondrial Localization Sequence Proximal to the N Terminus," Journal of Virology, 83(6):2601-2610.
Extended European Search Report dated Apr. 5, 2022 for EP 19849540.0.
Ryser et al., 2008, "mRNA Transfection of CXCR4-GFP Fusion-Simply Generated by PCR-Results in Efficient Migration of Primary Human Mesenchymal Stem Cells," Tissue Engineering Part C: Methods, 14(3):179-184.
Belmonte et al., "Digital PCR methods improve detection sensitivity and measurement precision of low abundance mtDNA deletions". Scientific reports. Apr. 28, 2016;6(1): pp. 1-11.
Chocron et al., "Cause or casualty: The role of mitochondrial DNA in aging and age-associated disease". Biochimica et Biophysica Acta (BBA)—Molecular Basis of Disease. Feb. 1, 2019; 1865(2): 285-97.
Extended European Search Report for European Application No. EP20878142.7 dated Oct. 18, 2023, 10 pages.
Floros et al., "Segregation of mitochondrial DNA heteroplasmy through a developmental genetic bottleneck in human embryos", Nature Cell Biology, Nature Publishing Group UK, London, vol. 20, No. 2, Jan. 15, 2018 (Jan. 15, 2018), pp. 144-151.
Tong et al., "Application of Digital PCR in Detecting Human Diseases Associated Gene Mutation", Cellular Physiology and Biochemistry, vol. 43, No. 4, Nov. 1, 2017 (Nov. 1, 2017), pp. 1718-1730.
Wang et al., "Noninvasive and accurate detection of hereditary hearing loss mutations with buccal swab based on droplet digital PCR". Analytical chemistry. Jul. 10, 2018; 90(15): 8919-26.
Wolf et al. "Principles of and strategies for germline gene therapy", Nature Medicine, Nature Publishing Group US, New York, vol. 25, No. 6, Jun. 1, 2019 (Jun. 1, 2019), pp. 890-897.

\* cited by examiner

Human Tcell vs EPC100 SNP assay Probe / Primer

| No. | Probe Name | Fluorescence | Sequence | Primer Name | Sequence |
|---|---|---|---|---|---|
| 1 | hTcell-probe | FAM | CAAcCAACCcTCAAC | HVR1-F-primer | CCCCATGCTTACAAGCAAGTAC |
|   | EPC100-probe | VIC | AGCAAtCAACCtTCAAC | HVR1-R-primer | TTGGAGTTGCAGTTGATGTGTG |

FIG. 9

METHODS FOR DETECTION OF MACRO-HETEROPLASMY AND MICRO-HETEROPLASMY IN MITOCHONDRIAL DNA

1. CROSS-REFERENCE TO RELATED APPLICATIONS

This application claims the benefit of priority of U.S. Provisional Application No. 62/925,677, filed Oct. 24, 2019, the entire contents of which is incorporated herein by reference.

2. SEQUENCE LISTING

The instant application contains a Sequence Listing which has been submitted in ASCII format via EFS-Web and is hereby incorporated by reference in its entirety. Said ASCII copy, created on Oct. 21, 2020, is named 14595-002-999 Sequence Listing.txt and is 6,264 bytes in size.

3. FIELD OF THE INVENTION

The present invention provides methods for detecting macro-heteroplasmy and/or micro-heteroplasmy in mitochondrial DNA.

4. BACKGROUND OF THE INVENTION

Mitochondrial diseases are a group of genetic heterogeneous disorders characterized by dysfunctional mitochondria. Currently, there are no curative options for patients suffering from mitochondrial disease, which leaves patients with only palliative care to relieve symptoms in patients (Gorman, G. S. et al. Mitochondrial diseases. Nat Rev Dis Primers 2, 16080, doi:10.1038/nrdp.2016.80 (2016))

Since the symbiosis of the progenitor of mitochondria and eukaryotes, alpha proteobacterium and archaea, respectively, an array of genes in mitochondria had been transferred into the nuclear genome that simultaneously evolved to acquire 200,000 fold expansion in the number of genes (Lane, N. & Martin, W. The energetics of genome complexity. Nature 467, 929-934, doi:10.1038/nature09486 (2010)).

Mitochondrial diseases can manifest from mutations in genes in the nuclear DNA (nDNA) and/or mitochondrial DNA (mtDNA) that encode structural mitochondrial proteins or proteins involved in mitochondrial function, and can affect any organ, develop at any age, and exhibit any severity (Lightowlers, R. N., Taylor, R. W. & Turnbull, D. M. Mutations causing mitochondrial disease: What is new and what challenges remain? Science 349, 1494-1499 (2015)). The phenotypic variability arising from a pathological mutation in mtDNA could be attributed to multiple copies of mtDNA. An individual cell possesses multiple copies of mitochondrial genome, ranging from 100,000 in an unfertilized oocyte to ~100 in sperm (Stewart, J. B. & Chinnery, P. F. The dynamics of mitochondrial DNA heteroplasmy: implications for human health and disease. Nat Rev Genet 16, 530-542, doi:10.1038/nrg3966 (2015)). Although there are some options for women with nuclear mutations that cause mitochondrial disease to have a child, such as prenatal and preimplantation genetic diagnosis, such options are not a solution for all women. Moreover, patients with pathogenic mitochondrial DNA mutations face many difficult challenges, because the inheritance pattern is so complicated by a genetic bottleneck and relaxed mtDNA replication (Wai, T., Teoli, D. & Shoubridge, E. A. The mitochondrial DNA genetic bottleneck results from replication of a subpopulation of genomes. Nature Genetics 40, 1484-1488, doi:10.1038/ng.258 (2008); Chinnery, P. F. & Samuels, D. C. Relaxed replication of mtDNA: a model with implications for the expression of disease. The American Journal of Human Genetics 64, 1158-1165 (1999)).

The mixture of mutated and wild-type genome is termed heteroplasmy (Holt, I. J., Harding, A. E. & Morgan-Hughes, J. A. Deletions of muscle mitochondrial DNA in patients with mitochondrial myopathies. Nature 331, 717-719, doi: 10.1038/331717a0 (1988)). It has been observed that the severity of mitochondrial disease often correlates with the level of heteroplasmy in the case of protein-coding gene mutations. Although a small ratio of mitochondrial genome with pathological mutations is pervasive, there seems to be a threshold to manifest the biochemical malfunction, typically 60 to 80% (Stewart, J. B. & Chinnery, P. F. The dynamics of mitochondrial DNA heteroplasmy: implications for human health and disease. Nat Rev Genet 16, 530-542, doi:10.1038/nrg3966 (2015)). For example, heteroplasmy less than 70% generally does not exhibit a clinical phenotype for the mitochondrial disease NARP (neurogenic muscle weakness, ataxia and retinitis pigmentosa), which is caused by mutation of MT-ATP6. In contrast, NARP exhibits symptoms where the heteroplasmy ranged from 70% to 90% and might remain stable into adult life. Extreme heteroplasmy (e.g., more than 90% heteroplasmy) results in Leigh syndrome (Tatuch, Y. et al. Heteroplasmic mtDNA mutation (T----G) at 8993 can cause Leigh disease when the percentage of abnormal mtDNA is high. American journal of human genetics 50, 852-858 (1992)).

However, heteroplasmy can not explain the variability of all mitochondrial diseases. For example, mtDNA mutations in tRNA genes manifest high clinical variability, which cannot be explained by heteroplasmy (Nunnari, J. & Suomalainen, A. Mitochondria: in sickness and in health. Cell 148, 1145-1159, doi:10.1016/j.cell.2012.02.035 (2012)). Moreover, ordinal methods for mitochondrial heteroplasmy are unable to discriminate between an intercellular homogenic population constituted from cells with similar intracellular heterogeneity for mtDNA and an intercellular heterogenic population constituted from cells with different rates of mutated mtDNA.

Thus, there is a significant unmet need to develop improved methods for determining heteroplasmy in a single cell.

5. SUMMARY OF THE INVENTION

In one aspect, provided herein is a method for detecting or monitoring the presence of mitochondrial DNA (mtDNA) heteroplasmy, comprising: (a) obtaining or having obtained a biological sample comprising one or more single cells; (b) determining an intracellular mtDNA sequence in said one or more single cells; (c) determining the proportion of wild-type and mutant forms of said intracellular mtDNA sequence in said one or more single cells; and (d) calculating an amount of intercellular and/or intracellular variability in the intracellular mtDNA sequence between and within said one or more single cells, thereby determining mtDNA heteroplasmy in said sample.

In another aspect, provided herein is a method for use in diagnosing a mitochondrial related disease or disorder in a subject based on the method comprising: (a) obtaining or having obtained a biological sample comprising one or more single cells from said subject; (b) determining an intracellular mitochondrial DNA (mtDNA) sequence in said one or more single cells; (c) determining the proportion of wild-type and mutant forms of said intracellular mtDNA sequence in said one or more single cells; (d) calculating an amount of intercellular and/or intracellular variability in the intracellular mtDNA sequence between and within said one or more single cells, thereby determining mtDNA heteroplasmy in said sample; and (e) diagnosing said subject as having or suspected of having a mitochondrial related disease or disorder if there is mtDNA heteroplasmy in said sample.

In yet another aspect, provided herein is a method for monitoring the efficacy of a therapy that affects mitochondrial DNA (mtDNA) in a subject having or suspected of having a mitochondrial related disease or disorder, comprising: (a) administering to said subject a therapy that affects mtDNA; (b) obtaining a biological sample comprising one or more single cells from said subject; (c) determining an intracellular mtDNA sequence in said one or more single cells; (d) determining the proportion of wild-type and mutant forms of said intracellular mtDNA sequence in said one or more single cells; (e) calculating an amount of intercellular and/or intracellular variability in the intracellular mtDNA sequence between and within said one or more single cells, thereby determining the level of mtDNA heteroplasmy in said sample; and (f) comparing the level of mtDNA heteroplasmy in said sample with the level of mtDNA heteroplasmy from a reference sample, wherein a change in the mtDNA heteroplasmy level is indicative of the efficacy of said therapy in said subject.

In some embodiments, the therapy that affects mtDNA is a mitochondrial replacement therapy. In some embodiments, the therapy that affects mtDNA is a mitochondrial replacement therapy. In specific embodiments, the therapy that affects mtDNA comprises administering a mitochondrial replaced cell (MirC). In some embodiments, the reference sample is obtained from the same subject prior to administering the therapy to the subject.

In another aspect, provided herein is a method of identifying a threshold level of heteroplasmy of a pathogenic mitochondrial DNA (mtDNA) mutation for use in stratifying a patient population having or suspected of having a mitochondrial related disease or disorder, comprising (a) obtaining or having obtained a biological sample comprising one or more single cells from a subject; (b) determining an intracellular mtDNA sequence in said one or more single cells; (c) determining the proportion of wild-type and mutant forms of said intracellular mtDNA sequence in said one or more single cells; (d) calculating an amount of intercellular and/or intracellular variability in the intracellular mtDNA sequence between and within said one or more single cells, thereby determining the level of mtDNA heteroplasmy in said sample; and (e) identifying the minimum level of heteroplasmy that specifically correlates with a mitochondrial disease or disorder, thereby determining said threshold level of heteroplasmy that manifests in said mitochondrial related disease or disorder.

In some embodiments of any of the methods provided herein, the method comprises calculating an amount of intercellular variability in the intracellular mtDNA sequence between said one or more single cells.

In some embodiments of any of the methods provided herein, the method comprises calculating an amount of intracellular variability in the intracellular mtDNA sequence within said one or more single cells.

In some embodiments of any of the methods provided herein, the method comprises calculating an amount of intercellular and intracellular variability in the intracellular mtDNA sequence between and within said one or more single cells.

In certain embodiments, determining the intracellular mtDNA sequence in said one or more single cells is performed in a single assay. In certain embodiments, determining the intracellular mtDNA sequence in said one or more single cells and determining the proportion of wild-type and mutant forms of said intracellular mtDNA sequence in said one or more single cells is performed in a single assay.

In some embodiments, determining the intracellular mtDNA sequence comprises a quantitative polymerase chain reaction (PCR) assay. In specific embodiments, the quantitative PCR assay is a digital droplet PCR (ddPCR) assay. In some embodiments, the quantitative PCR assay comprises TaqMan polymerase.

In some embodiments, the one or more single cells have homogenous intercellular mtDNA. In other embodiments, the one or more single cells have heterogeneous intercellular mtDNA. In some embodiments, the one or more single cells have heterogeneous intracellular mtDNA.

6. BRIEF DESCRIPTION OF THE FIGURES

Figure 5:
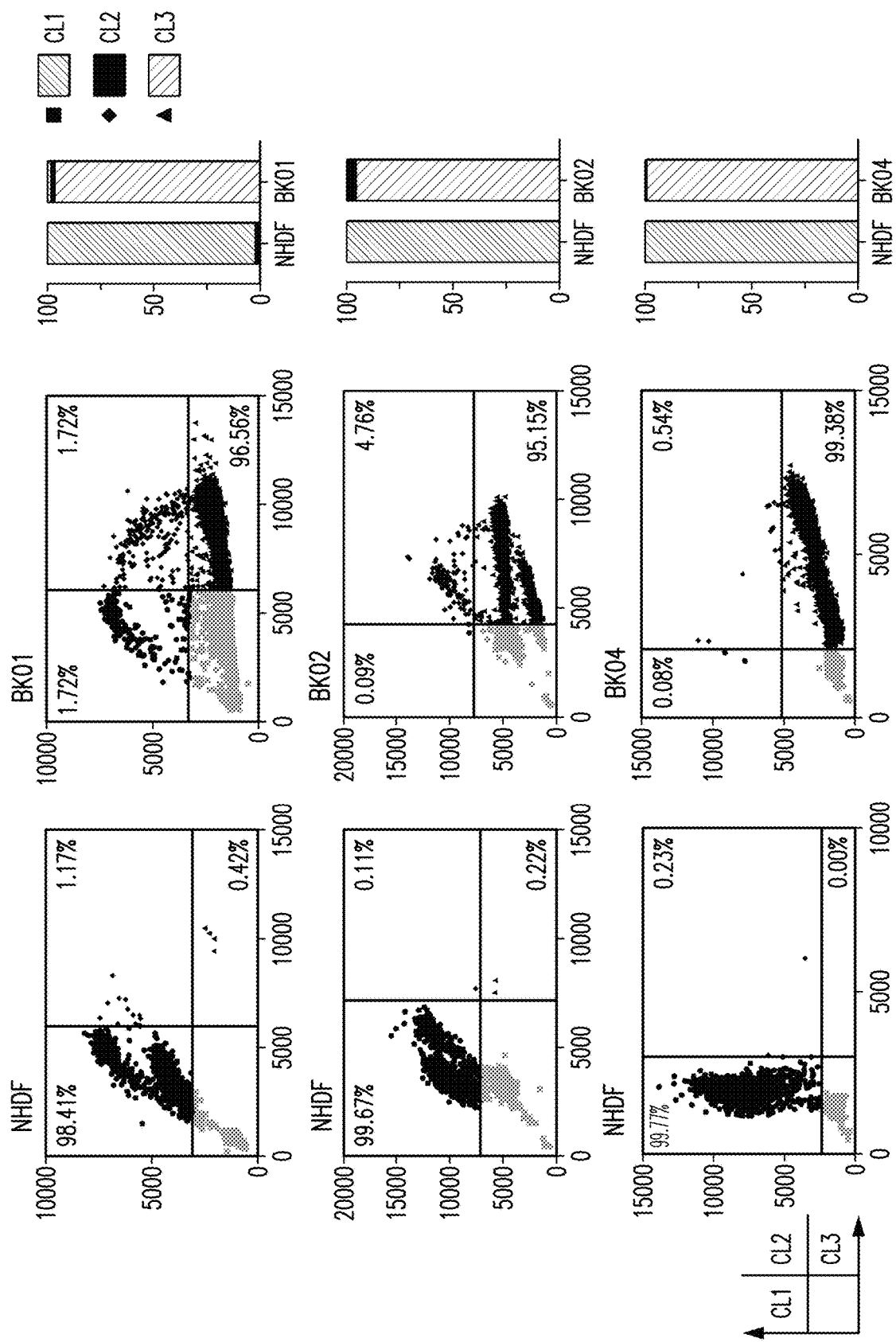

FIG. 5 illustrates the results of the ddPCR analysis at a single cell level. The healthy signal was plotted on the Y-axis and the mutant signal was plotted on the X-signal. The quadrant analysis shows cells possessing only mutant mtDNAs in lower right quadrant, cells possessing both mutant and healthy mtDNAs in upper right quadrant, and cells possessing only healthy mtDNA in upper left. The lower left quadrant exhibits droplets without a cell. The quadrant analysis in BK01 showed that a major part of cells, 96.56%, was homoplasmy in the mutant mtDNA plotted in lower right, but a minor part of cells had two kinds of mtDNA, the mutant and the healthy, plotted in upper right, which is the state of an intracellular heteroplasmy (FIG. 5, upper panel). Moreover, a population of cells constituted from sole healthy mtDNA existed at the same rate, 1.72%, as the cells with an intracellular heteroplasmy. BK02 contained the cell population with both the mutant and the healthy mtDNA plotted in upper right at the rate of 4.76% (FIG. 5, middle panel). BK04 showed the difference from the others in respect that there is only a single fraction of cells with sole mutated mtDNA (FIG. 5, lower panel). Both BK02 and BK04 did not contain a cell population with only the healthy mtDNA.

Figure 6:
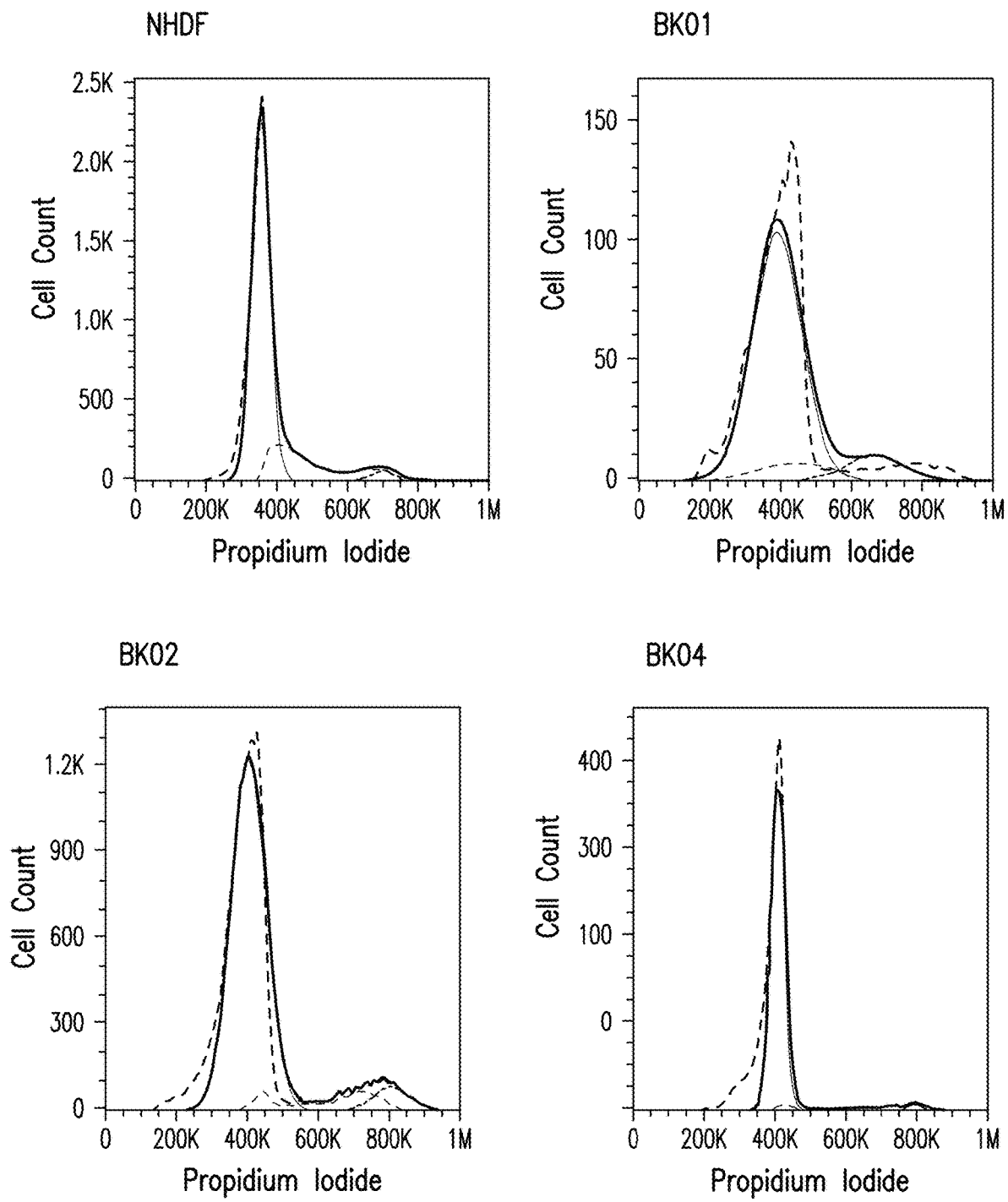
Figure 6:
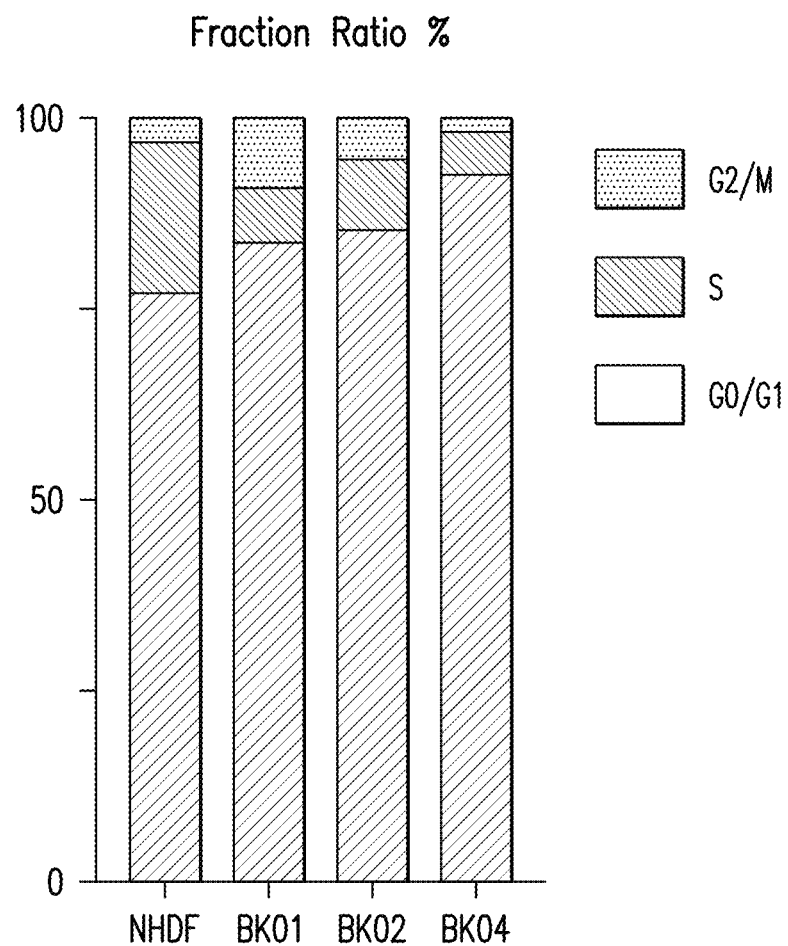

FIG. 6 illustrates cell cycle analysis for the three fibroblasts from patients with primary mitochondrial diseases (BK01, BK02, and BK04), relative to NHDF cells, and revealed that the fractions of S phase in these cells were less than half, compared with that in NHDF. The sum of G2/M and S phase ranged from 10 to 20% in diseased fibroblasts.

Figure 7:
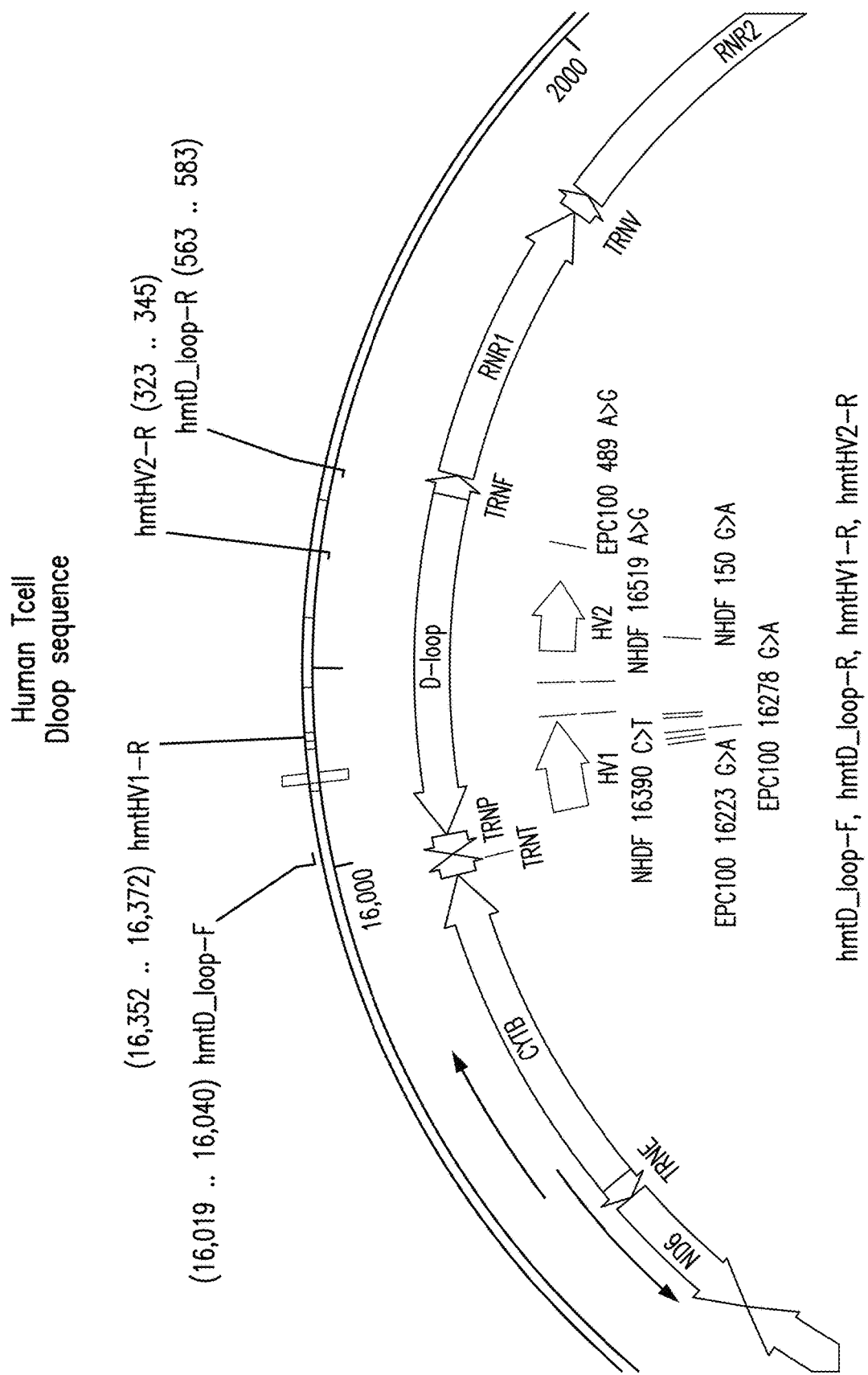

FIG. 7 illustrates the human T cell D-loop region used for sequencing mtDNA.

Figure 8:
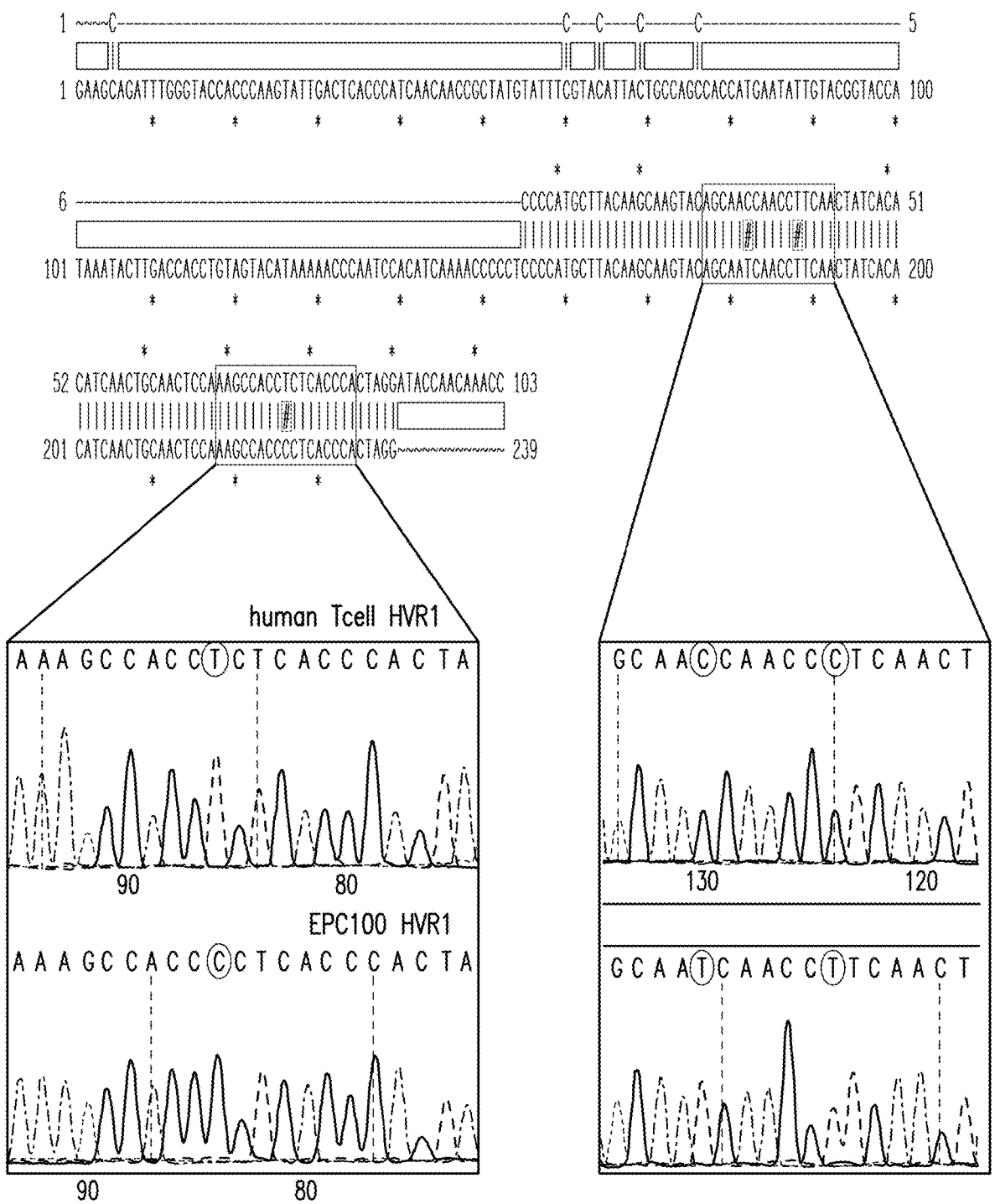

FIG. 8 illustrates the HVR1 mtDNA sequence in human T cells and EPC100 cells. SEQ ID NOs: 16 and 17 are depicted.

Figure 9:
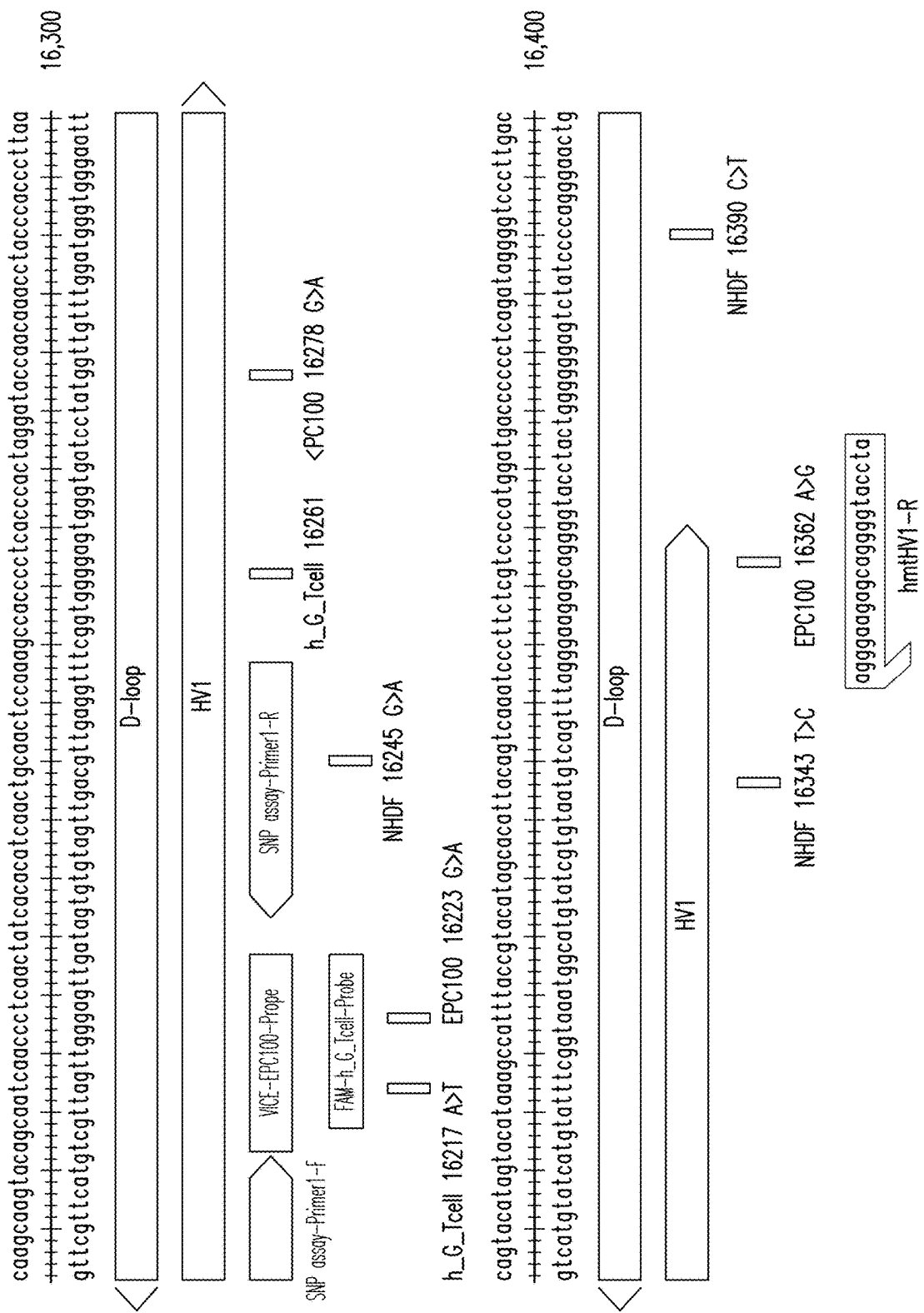

FIG. 9 illustrates human T cell vs EPC100 SNP assay Probe/Primer. SEQ ID NOs: 18-24 are depicted.

Figure 10:
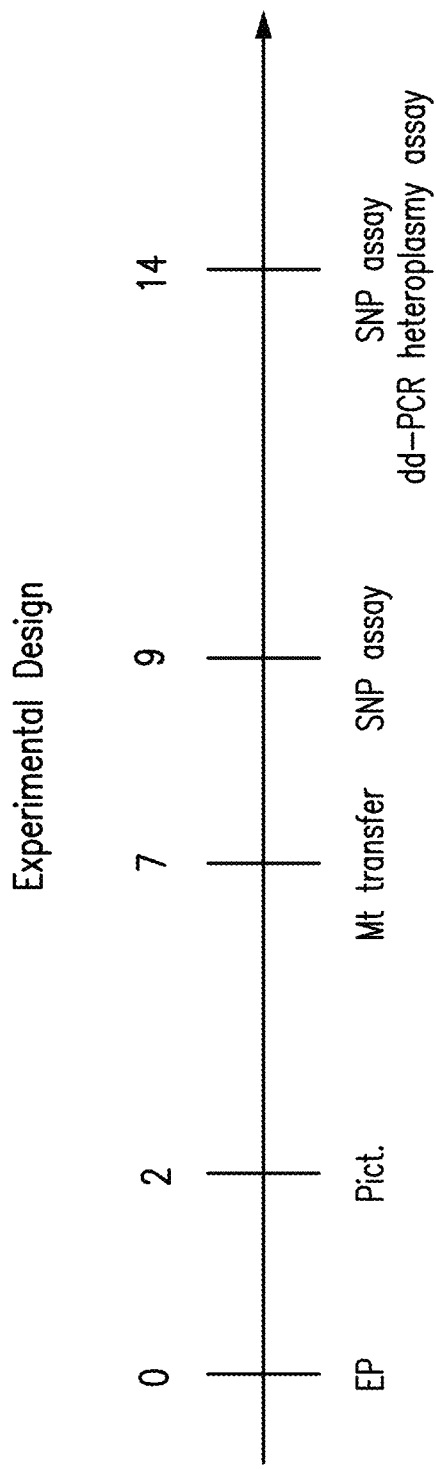

FIG. 10 illustrates the experimental design for the generation of MirC and the schedule of heteroplasmy assay.

Figure 11:
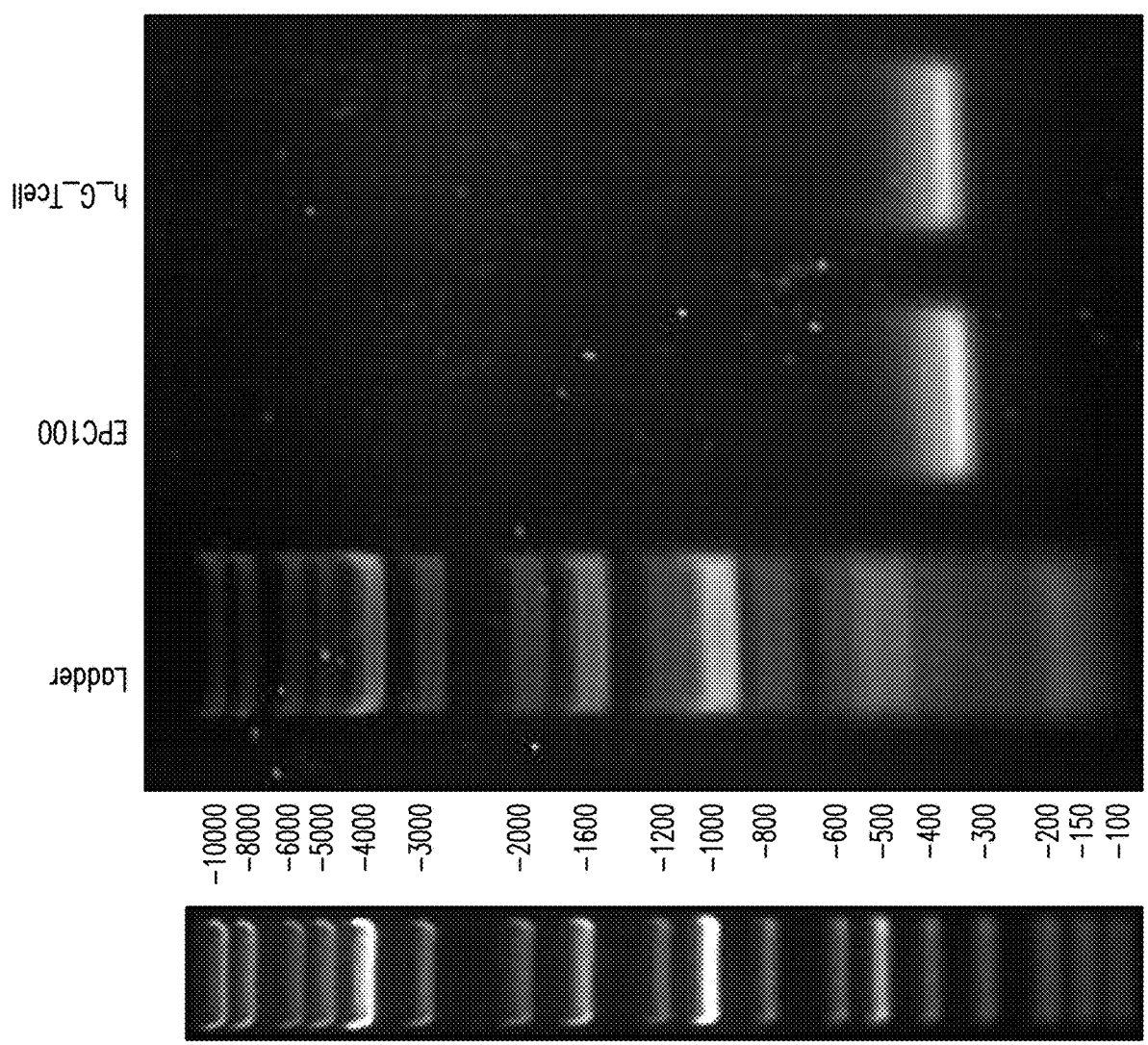

FIG. 11 illustrates PCR amplification product from human T cells and EPC100 cells.

Figure 12:
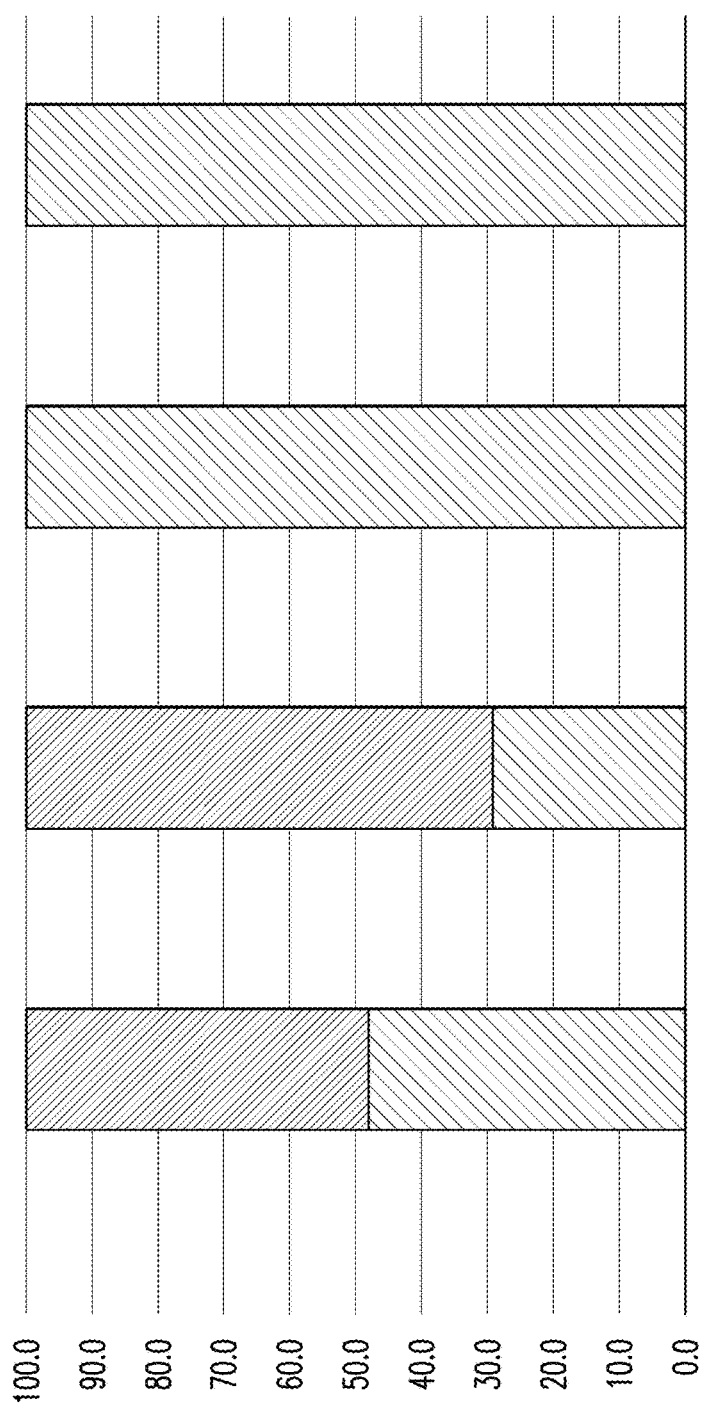
Figure 12:
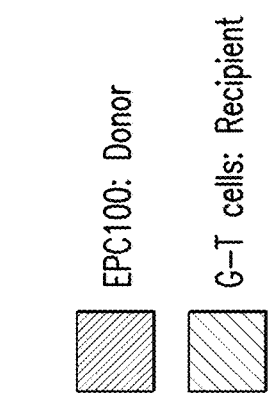
Figure 13:
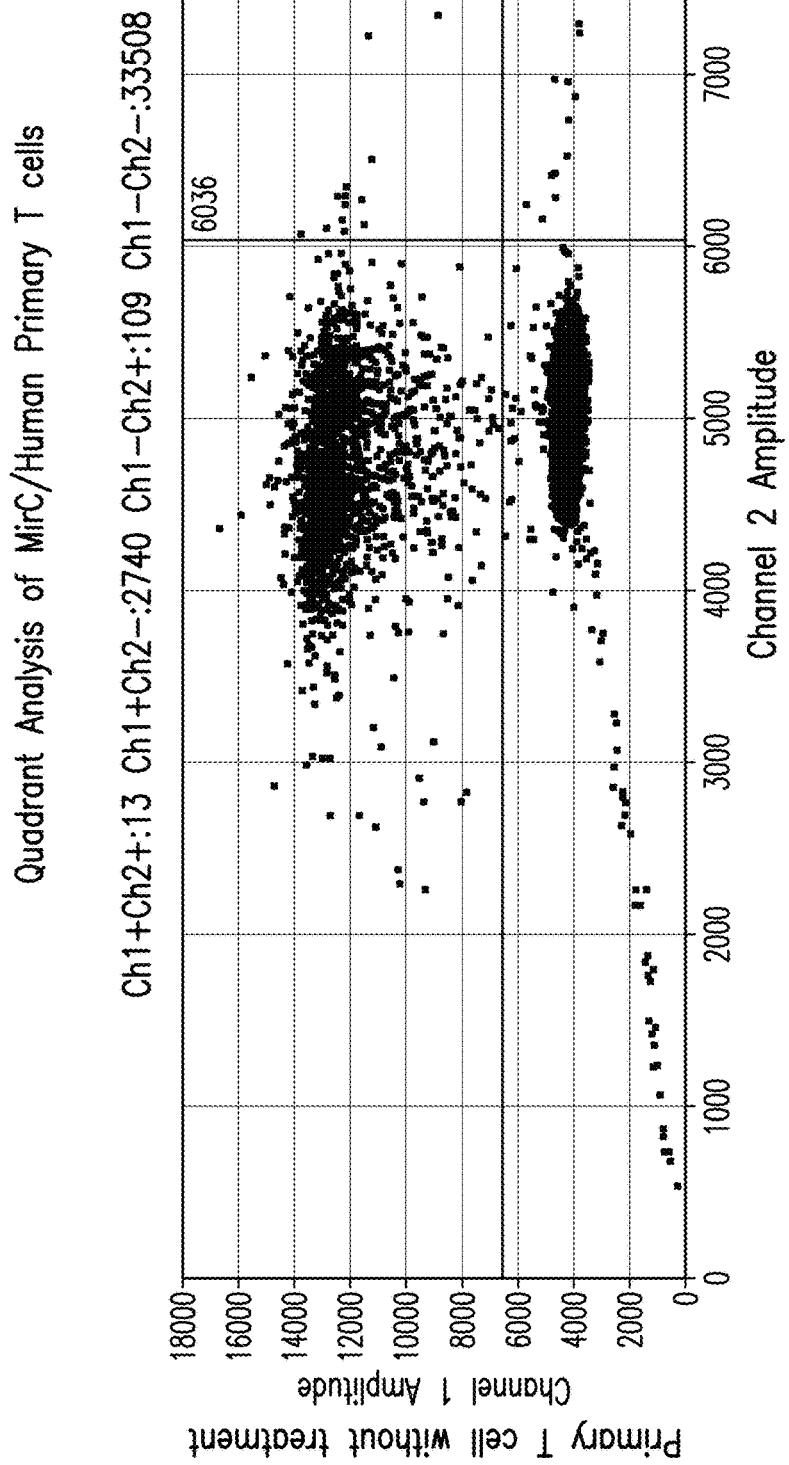
Figure 13:
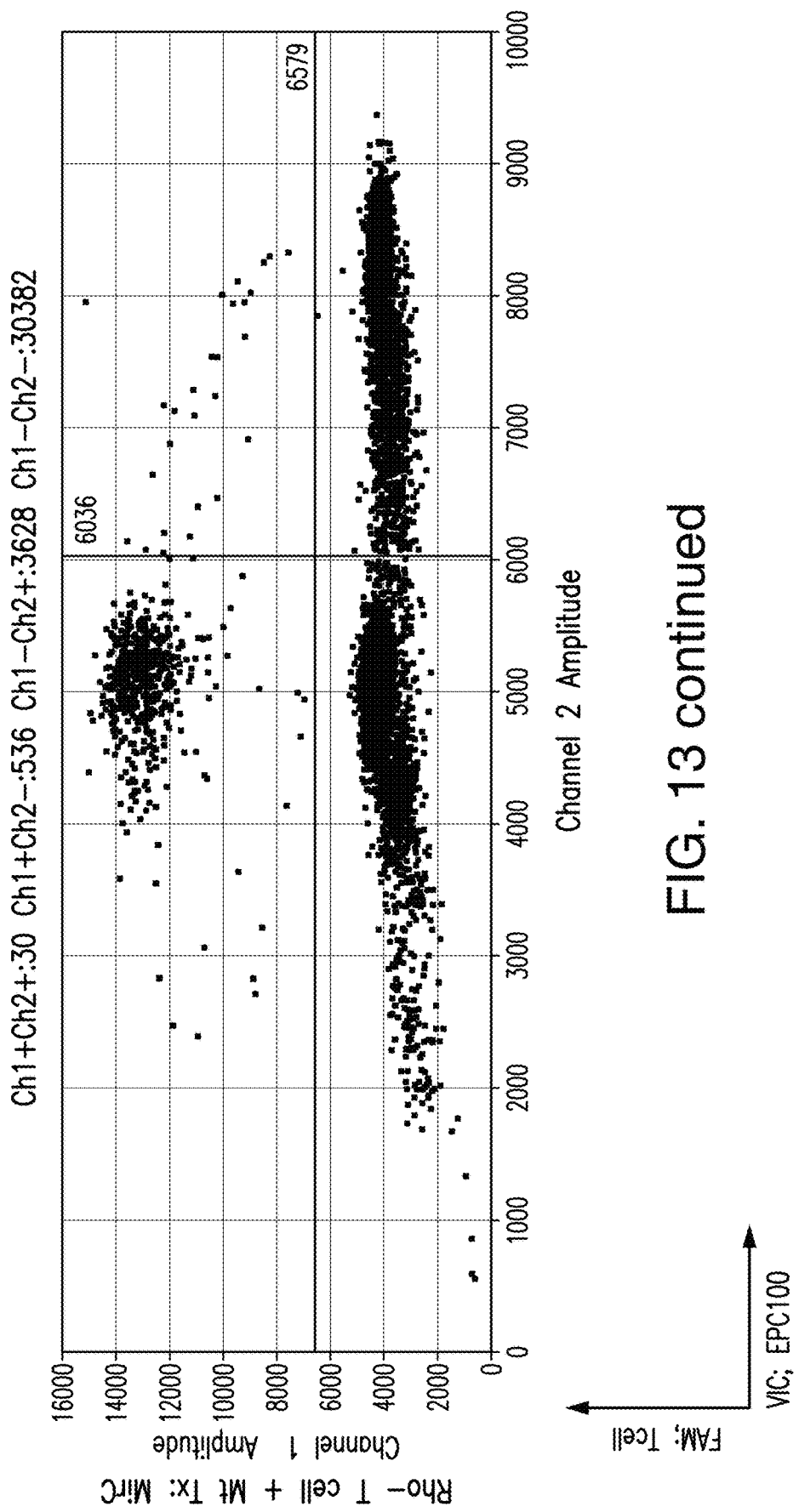

FIG. 12 illustrates quantification of TaqMan qPCR SNP genotyping assay for whole T cell population, with or without mitochondria replacement. Exogenous mtDNA occupied a half in 2 days, and about 70% in 7 days following the transfer, respectively FIG. 13 illustrates quadrant analysis of mitochondria replaced human primary T cells.

Figure 14:
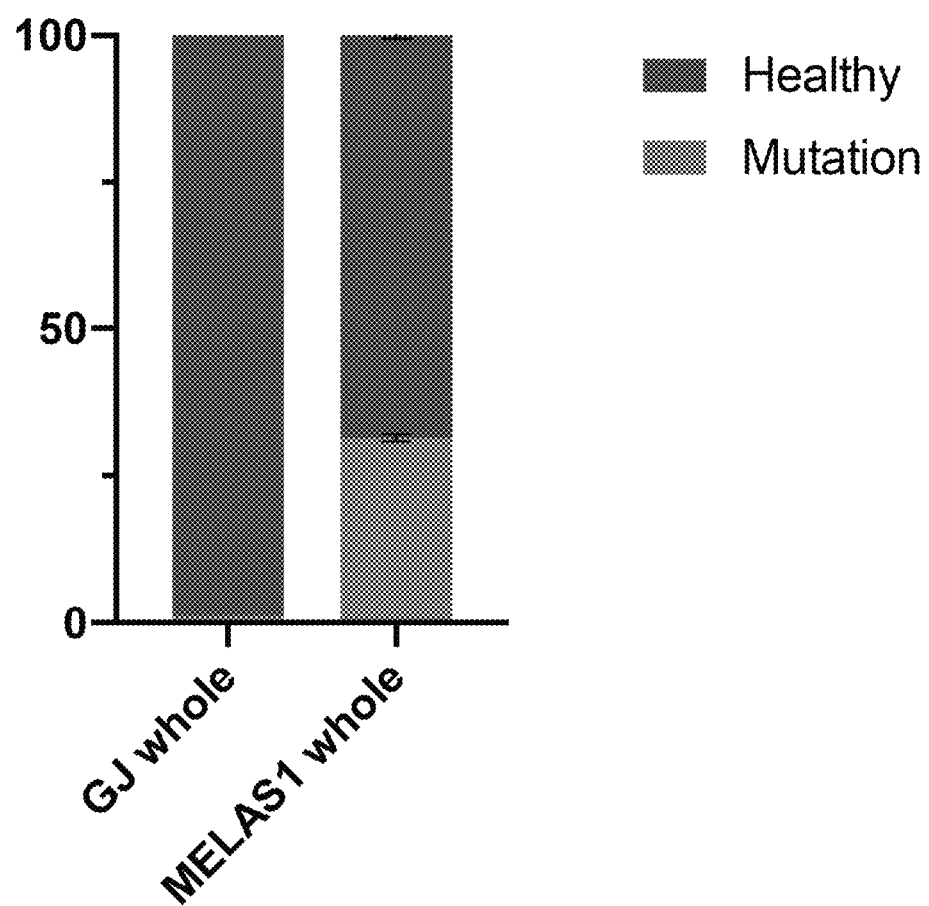

FIG. 14 illustrates gross heteroplasmy of mononuclear cells from a patient with MELAS compared to control GJ mononuclear cells as determined by TaqMan qPCR.

Figure 15:
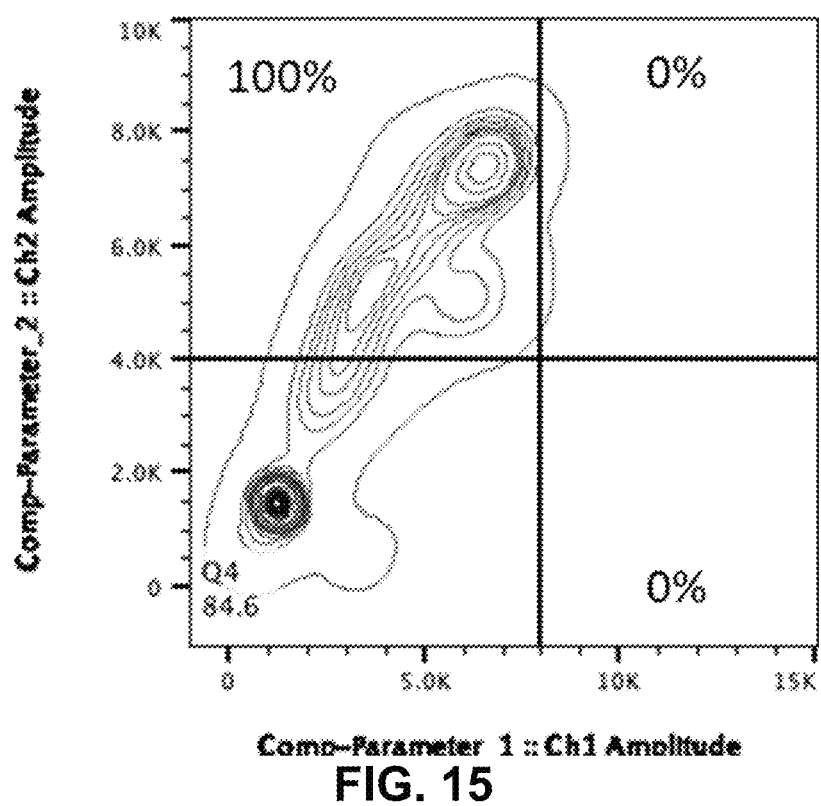

FIG. 15 illustrates exemplary results of sc-ddPCR analysis by FACs on control GJ mononuclear cells.

Figure 16:
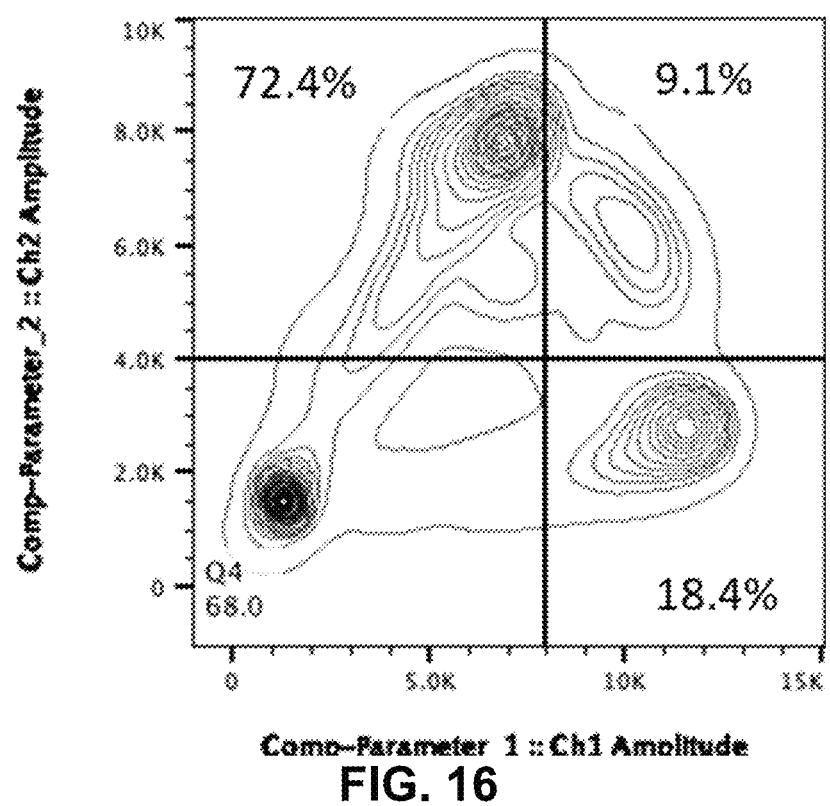

FIG. 16 illustrates exemplary results of sc-ddPCR analysis by FACs on control MELAS mononuclear cells.

Figure 17:
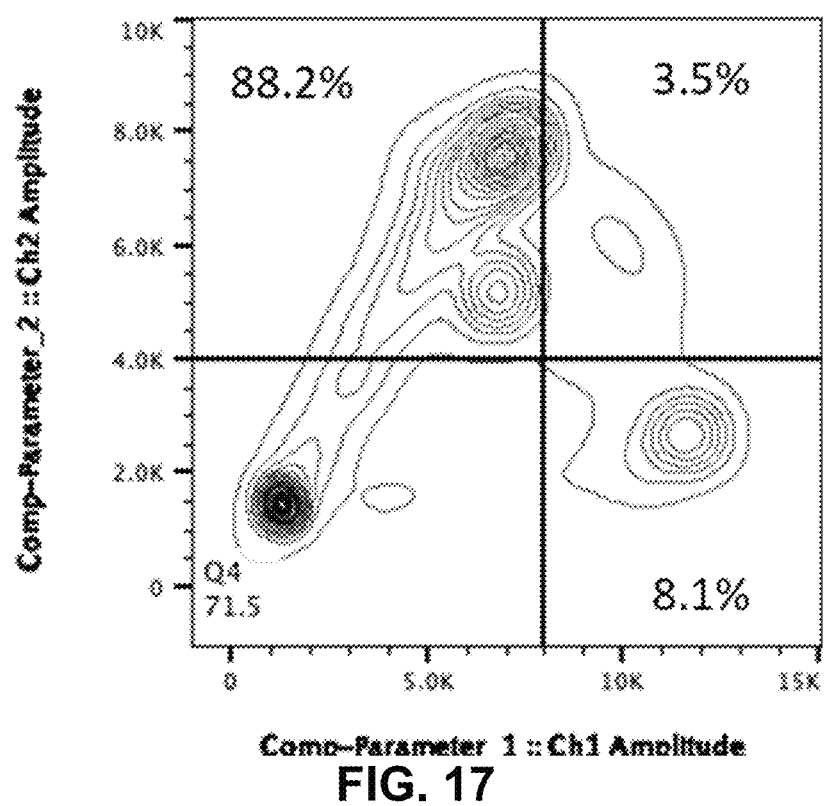

FIG. 17 illustrates exemplary results of sc-ddPCR analysis by FACs on control MELAS CD3+ T cells.

Figure 18:
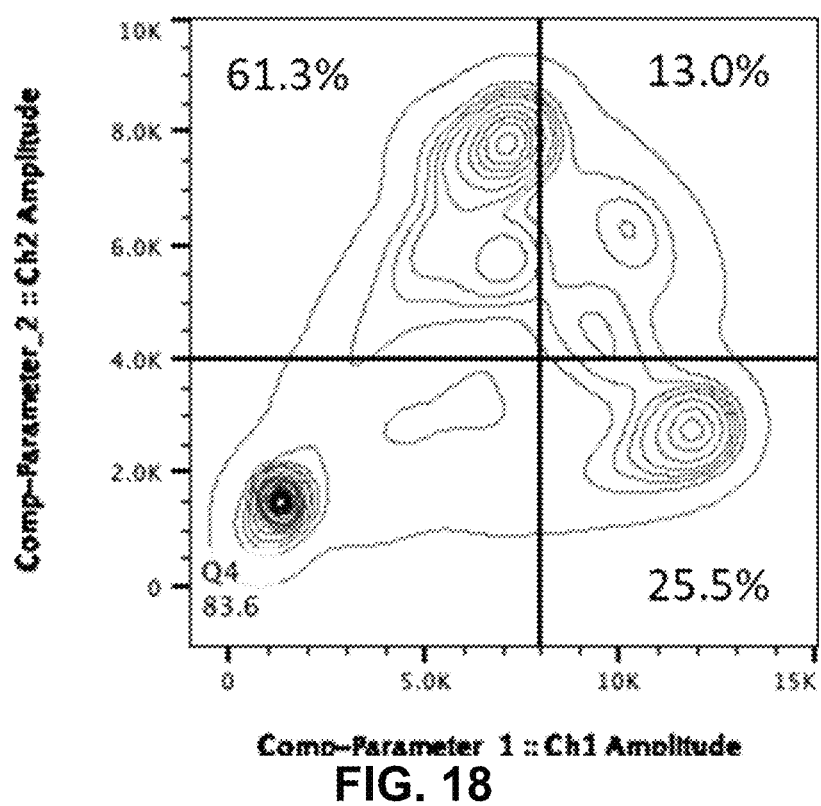

FIG. 18 illustrates exemplary results of sc-ddPCR analysis by FACs on control MELAS CD11b+ macrophage-monocyte lineage cells.

Figure 19:
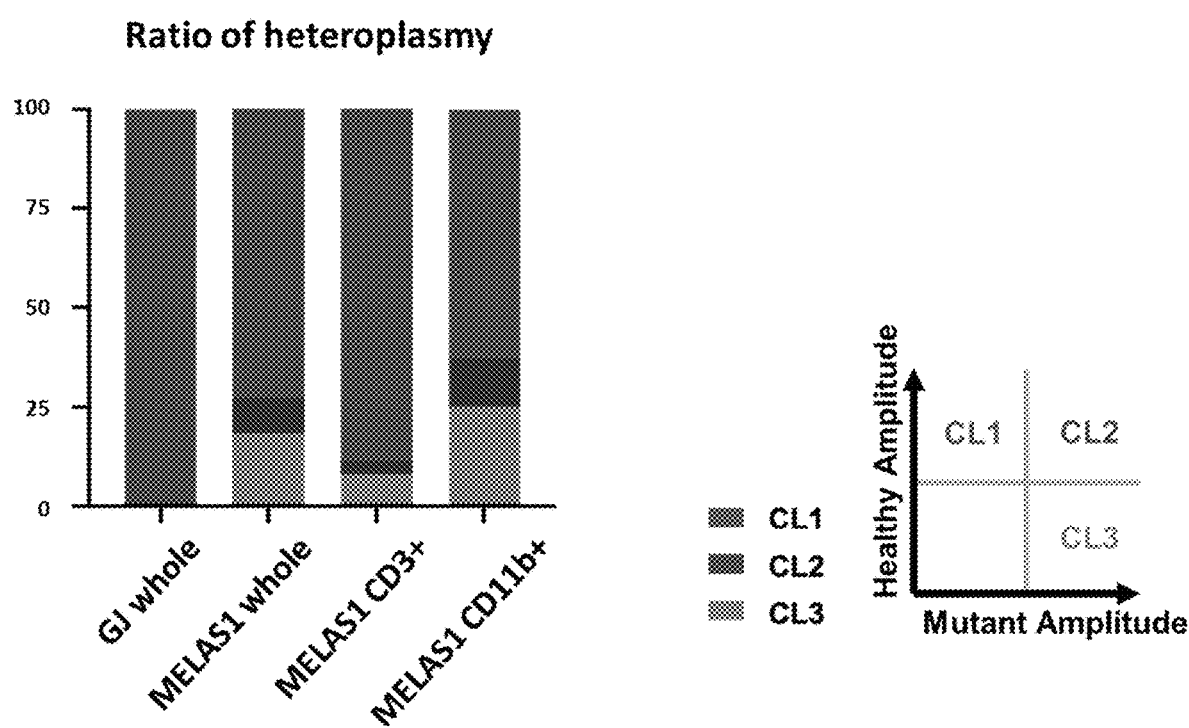

FIG. 19 illustrates a comparison of heteroplasmy of mononuclear cells, CD3+ T cells, and CD11b+ macrophage-monocyte lineage cells from a patient with MELAS compared to control GJ mononuclear cells.

7. DETAILED DESCRIPTION OF THE INVENTION

7.1 Definitions

Unless particularly defined otherwise, all terms including technical and scientific terms used in this application have the same meaning as commonly understood by one of ordinary skill in the art to which this invention belongs. In general, the nomenclatures used in this specification and the experimental methods described below are widely known and generally used in the related art.

As used herein, the term "mitochondria replaced cell" or MirC is intended to mean a cell having the substitution of endogenous mitochondria and/or mtDNA with exogenous mitochondria and/or mtDNA. For example, an exemplary mitochondria replaced cell (MirC) involves the substitution of endogenous mtDNA that encodes dysfunctional mitochondria, such as mtDNA originating from a subject having a mitochondrial disease or disorder, with exogenous mtDNA that encodes functional mitochondria, such as mtDNA originating from a healthy subject. Exemplary MirC can also include a cell with endogenous mitochondria substituted with exogenous mitochondria. However, it is understood that the substitution of the endogenous mitochondria and/or mtDNA can also include, for example, functional endogenous mtDNA from one cell, such as from an old cell, that is substituted with functional exogenous mtDNA from a different cell, such as from a healthier cell that is from a young subject. It is further understood that healthy endogenous mitochondria and/or mtDNA can also be substituted with dysfunctional exogenous mitochondria and/or exogenous mtDNA such as, for example, to mimic a mitochondrial disease or disorder.

As used herein, the terms "treat," "treating," and "treatment" refer to reduction in severity, progression, spread, and/or frequency of symptoms, elimination of symptoms and/or underlying cause, prevention of the occurrence of symptoms and/or their underlying cause, and improvement or remediation of damage. "Treatment" is meant to include therapeutic treatment as well as prophylactic, or suppressive measures for the condition, disease or disorder.

As used herein, the term "agent" when used in reference to depleting reducing mtDNA refers to an enzyme or compound that is capable of reducing mtDNA. Preferred agents include restriction enzymes, such as XbaI, that cleave mtDNA at one or more sites, without producing toxicity in the recipient cell. However, agents can also include an enzyme or compound that inhibit mtDNA synthesis or selectively promote degradation of the mitochondria.

As used herein, the terms "reduce," or "decrease" generally means a decrease of at least 5%, for example a decrease by at least about 10%, or at least about 20%, or at least about 30%, or at least about 40%, or at least about 50%, or at least about 60%, or at least about 70%, or at least about 80%, or at least about 90%, or any decrease between 5%-99% as compared to a reference level, as that term is defined herein. It is understood that a partial reduction or an agent that partially reduces endogenous mtDNA or decrease, as used herein, does not result in a complete depletion of all endogenous mtDNA (i.e., ρ0 cells). The term "increase" as used herein generally means an increase of at least 5%, for example an increase by at least about 10%, or at least about 20%, or at least about 30%, or at least about 40%, or at least about 50%, or at least about 60%, or at least about 70%, or at least about 80%, or at least about 90%, or more than 90%.

As used herein, the term "endogenous" refers to originating or derived internally. For example, endogenous mitochondria are mitochondria that are native to a cell.

As used herein, the term "exogenous" refers to cellular material (e.g., mitochondria or mtDNA) that is non-native to the host, such as cellular material that is derived externally. "Externally" typically means from a different source. For example, mitochondrial genomes are exogenous to host cells or host mitochondria when the mitochondrial genomes originate from different cell types or different species than the host cells or host mitochondria. In addition, "exogenous" can also refer to mitochondrial genomes that are removed from mitochondria, manipulated, and returned to the same mitochondria.

As used herein, the term "majority" is intended to mean the greatest amount, relative to the other amounts being compared. An exemplary majority when comparing two groups, is an amount that is any integer greater than about 50% or more, about 60% or more, about 70% or more, about 80% or more, or about 90% or more, or about 95% or more, of the total population, including any integer in-between. It is understood that the majority will depend on the total population being compared, and can be amounts lower than 50% when there are three or more groups being compared.

As used herein, the term "subject" is intended to mean a mammal. A subject can be a human or a non-human mammal, such as a dog, cat, bovid, equine, mouse, rat, rabbit, or transgenic species thereof. It is understood that a "subject" can also refer to a "patient," such as a human patient.

As used herein, the term "effective amount" refers to the amount of a composition of the invention effective to modulate, treat, or ameliorate any disease or disorder associated with heteroplasmy and/or dysfunctional mitochondria. As such, an effective amount can include, for example, a therapeutically effective amount, which refers to an effective amount in a therapy, or a biologically effective amount, which refers to an effective amount for a biological effect. The terms "therapeutically effective amount" and "effective amount" can encompass an amount that improves overall therapy, reduces or avoids symptoms or causes of disease or disorder, or enhances the therapeutic efficacy of another therapeutic agent. The amount of a given composition that will correspond to such an amount will vary depending upon various factors, such as the given composition, the pharmaceutical formulation, the route of administration, the type of condition, disease or disorder, the identity of the subject or host being treated, and the like, but can nevertheless be routinely determined by one skilled in the art. As defined herein, a therapeutically effective amount of an agent may be readily determined by one of ordinary skill by routine methods known in the art.

As used herein, the term "age-related disease" refers to any number of conditions attributable to advancement in age. These conditions include, without limitation, osteoporosis, bone loss, arthritis, stiffening joints, cataracts, macular degeneration, metabolic diseases including diabetes mellitus, neurodegenerative diseases including Alzheimer's Disease and Parkinson's Disease, immunosenescence, and heart disease including atherosclerosis and dyslipidemia. The phrase "age related disease" further encompasses neurodegenerative diseases, such as Alzheimer's Disease and related disorders, ALS, Huntington's disease, Parkinson's Disease, and cancer.

As used herein, the term "autoimmune disease" is intended to mean a disease or disorder arising from immune reactions directed against an individual's own tissues, organs or a manifestation thereof or a resulting condition therefrom. An autoimmune disease can refer to a condition that results from, or is aggravated by, the production of autoantibodies that are reactive with an autoimmune antigen or epitope thereof. An autoimmune disease can be tissue- or organ-specific, or it can be a systemic autoimmune disease. Systemic autoimmune diseases include connective tissue diseases (CTD), such as systemic lupus erythematosus (lupus; SLE), mixed connective tissue disease systemic sclerosis, polymyositis (PM), dermatomyositis (DM), and Sjögren's syndrome (SS). Additional exemplary autoimmune diseases further include rheumatoid arthritis, and anti-neutrophil cytoplasmic antibody (ANCA) polyangiitis.

As used herein, the term "genetic disease" refers to a disease caused by an abnormality, such as a mutation, in the nuclear genome. Exemplary genetic diseases include, but are not limited to, Hutchinson-Gilford Progeria Syndrome, Werner Syndrome, and Huntington's disease.

As used herein, the term "cancer" includes but is not limited to, solid cancer and blood borne cancer. The terms "cancer" and "cancerous" refer to or describe the physiological condition in mammals that is typically characterized by unregulated cell growth.

As used herein, the terms "mitochondrial disease or disorder" and "mitochondrial disorder" are interchangeable and refer to a group of conditions caused by inherited or acquired damage to the mitochondria causing an energy shortage within those areas of the body. Exemplary organs effected by mitochondrial disease or disorder include those that consume large amounts of energy such as the liver, muscles, brain, eye, ear, and the heart. The result is often liver failure, muscle weakness, fatigue, and problems with the heart, eyes, and various other systems.

As used herein, the term "mitochondrial DNA abnormalities" refer to mutations in mitochondrial genes whose products localize to the mitochondrion, and not observed in the cells of healthy subjects. Exemplary diseases associated with mitochondrial DNA abnormalities include, for example, chronic progressive external ophthalmoplegia (CPEO), Pearson syndrome, Kearns-Sayre syndrome (KSS), diabetes and deafness (DAD), leber hereditary optic neuropathy (LHON), LHON-plus, neuropathy, ataxia, and retinitis pigmentosa syndrome (NARP), maternally-inherited Leigh syndrome (MILS) also known as Leigh syndrome caused by mutant mtDNA, mitochondrial encephalomyopathy, lactic acidosis, and stroke-like episodes (MELAS), myoclonic epilepsy and ragged-red fiber disease (MERRF), familial bilateral striatal necrosis/striatonigral degeneration (FBSN), Luft disease, aminoglycoside-induced Deafness (AID), and multiple deletions of mitochondrial DNA syndrome.

As used herein, the term "nuclear DNA abnormalities" within the context of mitochondrial disease or disorder refer to mutations or changes in the coding sequence of nuclear genes whose products localize to the mitochondrion. Exemplary mitochondrial disease or disorders associated with nuclear mutations include Mitochondrial DNA depletion syndrome-4A, mitochondrial recessive ataxia syndrome (MIRAS), mitochondrial neurogastrointestinal encephalomyopathy (MNGIE), mitochondrial DNA depletion syndrome (MTDPS), DNA polymerase gamma (POLG)-related disorders, sensory ataxia neuropathy dysarthria ophthalmoplegia (SANDO), leukoencephalopathy with brainstem and spinal cord involvement and lactate elevation (LBSL), co-enzyme Q10 deficiency, Leigh syndrome (caused by nuclear mutations), mitochondrial complex abnormalities, fumarase deficiency, α-ketoglutarate dehydrogenase complex (KGDHC) deficiency, succinyl-CoA ligase deficiency, pyruvate dehydrogenase complex deficiency (PDHC), pyruvate carboxylase deficiency (PCD), carnitine palmitoyltransferase I (CPT I) deficiency, carnitine palmitoyltransferase II (CPT II) deficiency, carnitine-acyl-carnitine (CACT) deficiency, autosomal dominant-/autosomal recessive-progressive external ophthalmoplegia (ad-/ar-PEO), infantile onset spinal cerebellar atrophy (IOSCA), mitochondrial myopathy (MM) spinal muscular atrophy (SMA), growth retardation, aminoaciduria, cholestasis, iron overload, early death (GRACILE), and Charcot-Marie-Tooth disease type 2A (CMT2A).

As used herein, the term "dysfunctional mitochondria" refer to mitochondria that are in opposition to functional mitochondria. Exemplary dysfunctional mitochondria include mitochondria that are incapable of synthesizing or synthesize insufficient amounts of ATP by oxidative phosphorylation. As used herein, the term "functional mitochondria" refers to mitochondria that consume oxygen and produce ATP.

As used herein, the term "mutation" refers to any changing of the structure of a gene, resulting in a variant (also called "mutant") form. Mutations in a gene may be caused by the alternation of single base in DNA, or the deletion, insertion, or rearrangement of larger sections of genes or chromosomes. In some embodiments, the mutation can affect the function or the resulting protein. For example, a mutation in a single nucleotide of DNA (i.e., point mutation) in the coding region of a protein can result in a codon that encodes for a different amino acid (i.e., missense mutation). It is understood that this different amino acid can alter the structure of the protein, and that in certain circumstances, as described herein, can alter the function of the organelle, such as the mitochondrion.

As used herein, the terms "heteroplasmy" and "heteroplasmic" refer to the occurrence of more than one type of mitochondrial DNA genome in an individual or sample. Varying degrees of heteroplasmy are associated with varying degrees of the physiological conditions described herein. Heteroplasmy may be identified by means known to the art, and the severity of the physiological condition associated with specific nucleotide alleles is expected to vary with the percentage of such associated alleles within the individual.

As used herein, the term "wild-type" when used in the context of mitochondrial DNA refers to the genotype of the typical form of a species as it occurs in nature. An exemplary reference genome for the wild-type human mtDNA genome includes the Cambridge Reference Sequence (CRS).

As used herein, the terms "about" or "approximately" when used in conjunction with a number refer to any number within 1, 5, 10, 15 or 20% of the referenced number.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following? Sambrook et al., Molecular Cloning: A Laboratory Manual, Third Ed., Cold Spring Harbor Laboratory, New York (2001); Ausubel et al., Current Protocols in Molecular Biology, John Wiley and Sons, Baltimore, Md. (1999); Glover, ed., DNA Cloning, Volumes I and II (1985); Gait, ed., Oligonucleotide Synthesis (1984); Hames & Higgins, eds., Nucleic Acid Hybridization (1984); Hames & Higgins, eds., Transcription and Translation (1984); Freshney, ed., Animal Cell Culture: Immobilized Cells and Enzymes (IRL Press, 1986); Källen et al, Plant Molecular Biology—A Laboratory Manual (Ed. by Melody S. Clark; Springer-Verlag, 1997); Immunochemical Methods in Cell and Molecular Biology (Academic Press, London); Scopes, Protein Purification: Principles and Practice (Springer Verlag, N.Y., 2d ed. 1987); and Weir & Blackwell, eds., Handbook of Experimental Immunology, Volumes I-IV (1986).

7.2 Mechanistic Insights

The heteroplasmy in either dividing cells or non-dividing cells changes with time via various mechanism, which affects the development and the progression in the disease. A proposed mechanism to change the heteroplasmy is a vegetative segregation, in which model proliferated mitochondria are randomly and unequally distributed into daughter cells, and the proportion of wild-type to mutated mtDNA occasionally deviates to either the former or the latter through random genetic drift (Birky, C. W., Maruyama, T. & Fuerst, P. An Approach To Population And Evolutionary Genetic Theory For Genes In Mitochondria And Chloroplasts, And Some Results. Genetics 103, 513 (1983)). Another is a relaxed replication, in which model mitochondria are selected for replication and destruction at random, and independently from the cell cycle in the host, whose genome is stringently regulated to replicate synchronously to a cell division (Birky Jr, C. Relaxed and stringent genomes: why cytoplasmic genes don't obey Mendel's laws. Journal of Heredity 85, 355-365 (1994)). These neutral genetic drifts are influenced by either positive or negative selection pressure. A long deletion mutation of mtDNA with a pathogenic consequence exhibits a replicative advantage and outnumber the wild-type genome (Clark, K. A. et al. Selfish little circles: transmission bias and evolution of large deletion-bearing mitochondrial DNA in *Caenorhabditis briggsae* nematodes. PLoS One 7, e41433, doi:10.1371/journal.pone.0041433 (2012)). Given that wild-type mtDNA is quantitatively regulated in an individual cell, the occurrence of a mutation in mtDNA promote to proliferate mitochondria either with or without the mutation in mtDNA, termed maintenance of wild-type theory (Durham, S. E., Brown, D. T., Turnbull, D. M. & Chinnery, P. F. Progressive depletion of mtDNA in mitochondrial myopathy. Neurology 67, 502-504 (2006)), which reinforce a positive selection under the replicative advantage of the mutation. To the contrary, the unfavorable biochemical features in a pathogenic mutation lead to less survive for hematopoietic stem or progenitor cells, resulted in loss of the mtDNA mutation in blood (Rajasimha, H. K., Chinnery, P. F. & Samuels, D. C. Selection against pathogenic mtDNA mutations in a stem cell population leads to the loss of the 3243A-->G mutation in blood. Am J Hum Genet 82, 333-343, doi:10.1016/j.ajhg.2007.10.007 (2008)).

As an extreme case of mitochondrial diseases, mtDNA maintenance defects, which are caused by the mutations of 20 nuclear genes, generate an array of diseases based on resultant mtDNA depletion or multiple mtDNA deletions (El-Hattab, A. W., Craigen, W. J. & Scaglia, F. Mitochondrial DNA maintenance defects. Biochim Biophys Acta Mol Basis Dis 1863, 1539-1555, doi:10.1016/j.bbadis.2017.02.017 (2017)). The targets to be involved in specifically terminal differentiated cells, such as neuron and skeletal muscle, not proliferating cells that possess up to 1,000-fold higher nucleotide pool in the cytosol, such as hematological cells and fibroblasts (Gorman, G. S. et al. Mitochondrial diseases. Nat Rev Dis Primers 2, 16080, doi:10.1038/nrdp.2016.80 (2016)). Considered the treatment for mitochondrial diseases, we are required to develop a companion diagnostic, as anti-cancer drug targeted to a specific molecule have it to assist the judgement for the indication (Jorgensen, J. T. Companion and complementary diagnostics: clinical and regulatory perspectives. Trends in cancer 2, 706-712 (2016)).

Although recent advances in biomarker for mitochondria have established the effectiveness of fibroblast growth factor 21 (FGF21) with a sensitivity and specificity of 92% (Suomalainen, A. et al. FGF-21 as a biomarker for muscle-manifesting mitochondrial respiratory chain deficiencies: a diagnostic study. The Lancet Neurology 10, 806-818, doi:10.1016/s1474-4422(11)70155-7 (2011)), and growth/differentiation factor 15 (GDF15) with a sensitivity of 98% and a specificity of 86% (Yatsuga, S. et al. Growth differentiation factor 15 as a useful biomarker for mitochondrial disorders. Ann Neurol 78, 814-823, doi:10.1002/ana.24506 (2015)), the regain of wild-type mtDNA and the remove of mutation burden in affected cells should be an optimal indicator for a successful cure. The heteroplasmy should be useful not only for a diagnosis to mitochondrial diseases, but also for an estimation for the effectiveness in treatment process.

7.3 Intercellular Heteroplasmy Vs Intracellular Heteroplasmy

Mitochondrial genotypic heterogeneity was redefined to micro-heteroplasmy that intracellular mutations in mtDNA exists in a single cell, and macro-heteroplasmy that intercellular mutations in mtDNA exists among supposedly identical cells, in addition to the difference of mtDNA copy number in an individual cell (Aryaman, J., Johnston, I. G. &

Jones, N. S. Mitochondrial Heterogeneity. Front Genet 9, 718, doi:10.3389/fgene.2018.00718 (2018)). Micro-heteroplasmy may give rise to macro-heteroplasmy, whereas macro-heteroplasmy may be the consequence to group different homogeneous cell population with respect to mtDNA, which possess either wild-type or mutated genome.

Micro-heteroplasmy occurs by replication errors, rather than oxidative damage (Kauppila, J. H. & Stewart, J. B. Mitochondrial DNA: Radically free of free-radical driven mutations. Biochim Biophys Acta 1847, 1354-1361, doi: 10.1016/j.bbabio.2015.06.001 (2015)). Single-mitochondrion sequencing in neuron supposed the mechanism for negative selection could be present to negate micro-heteroplasmy, whereas several mutations exhibited to dominate more than 90% in a single cell, suggesting the existence for a mechanism to circumvent the negative selection (Morris, J. et al. Pervasive within-Mitochondrion Single-Nucleotide Variant Heteroplasmy as Revealed by Single-Mitochondrion Sequencing. Cell Rep 21, 2706-2713, doi:10.1016/j.celrep.2017.11.031 (2017)). It remains to be solved that the wide spread of the mutations could be achieved and whether the mechanism could attribute to pathological outcome.

On the other hand, macro-heteroplasmy could arise through neutral genetic drift (Wonnapinij, P., Chinnery, P. F. & Samuels, D. C. The distribution of mitochondrial DNA heteroplasmy due to random genetic drift. Am J Hum Genet 83, 582-593, doi:10.1016/j.ajhg.2008.10.007 (2008)), and demonstrate high mutation levels that are involved in diseases (Rossignol, R. et al. Mitochondrial threshold effects. The Biochemical journal 370, 751-762, doi:10.1042/BJ20021594 (2003)). The variance of macro-heteroplasmy due to neutral genetic drift is mathematically predicted to increases with time, mitophagy rate, and network fragmentation (Aryaman, J., Bowles, C., Jones, N. S. & Johnston, I. G. Mitochondrial network fragmentation modulates mutant mtDNA accumulation independently of absolute fission-fusion rates. bioRxiv, 409128, doi:10.1101/409128 (2018)), but to decrease with total mtDNA copy number (Chinnery, P. F. & Samuels, D. C. Relaxed replication of mtDNA: a model with implications for the expression of disease. The American Journal of Human Genetics 64, 1158-1165 (1999)). During development, mitochondrial bottleneck characterized by the reduction of mtDNA copy number increases heteroplasmy variance, resulted in the elimination of cells with mutation load over the threshold (Cree, L. M. et al. A reduction of mitochondrial DNA molecules during embryogenesis explains the rapid segregation of genotypes. Nat Genet 40, 249-254, doi:10.1038/ng.2007.63 (2008)). A child bearing high pathogenic heteroplasmy variance could develop either a mitochondrial disease or a disorder not to be considered a direct correlation with mitochondrial dysfunction in later lifetime. The mutation accumulations in mtDNA could be recognized not only in neurodegenerative disease, Parkinson disease, but also in the physiological aging process (Bender, A. et al. High levels of mitochondrial DNA deletions in substantia nigra neurons in aging and Parkinson disease. Nat Genet 38, 515-517, doi:10.1038/ng1769 (2006)).

Mitophagy is activated by a variety of mitochondrial stress, such as nutrient deprivation, hypoxia, and oxidative stress, to which mutation loads relate (Wei, H., Liu, L. & Chen, Q. Selective removal of mitochondria via mitophagy: distinct pathways for different mitochondrial stresses. Biochim Biophys Acta 1853, 2784-2790, doi:10.1016/j.bbamcr.2015.03.013 (2015)). Mitochondrial dynamics, fusion and fission, play an essential role to maintain their function and quality (Sebastian, D., Palacin, M. & Zorzano, A. Mitochondrial Dynamics: Coupling Mitochondrial Fitness with Healthy Aging. Trends Mol Med 23, 201-215, doi:10.1016/j.molmed.2017.01.003 (2017)). Fragmented mitochondria, which their membrane potentials are depolarized, are preferentially degraded via mitophagy (Twig, G. et al. Fission and selective fusion govern mitochondrial segregation and elimination by autophagy. The EMBO Journal 27, 433-446, doi:10.1038/sj.emboj.7601963 (2008)). Mitophagy might promote mtDNA turnovers to increase and maintain the heteroplasmy variance in mitochondrial disease and aging, rather than negative pressure to mutation loads (Aryaman, J., Johnston, I. G. & Jones, N. S. Mitochondrial Heterogeneity. Front Genet 9, 718, doi:10.3389/fgene.2018.00718 (2018)). So far, the estimation of mutation loads has been executed in bulk cellular samples, such as peripheral bloods and skeletal muscle biopsy. The measurement can't discriminate micro-heteroplasmy and macro-heteroplasmy. In order to understand cellular events due to a mutation load, a single cell analysis must be required in various biological processes with the mutation load.

7.4 Detection System

There are a lot of methods to detect and genotype DNA sequence variances, including single nucleotide polymorphisms (SNPs), which have been utilized in the field of diagnostics for cancer, genetic disorders, and infectious diseases (Angulo, B., Lopez-Rios, F. & Gonzalez, D. A new generation of companion diagnostics: cobas BRAF, KRAS and EGFR mutation detection tests. Expert Review of Molecular Diagnostics 14, 517-524, doi:10.1586/14737159.2014.910120 (2014); Urata, M. et al. High-sensitivity detection of the A3243G mutation of mitochondrial DNA by a combination of allele-specific PCR and peptide nucleic acid-directed PCR clamping. Clin Chem 50, 2045-2051, doi:10.1373/clinchem.2004.033761 (2004); Payungporn, S., Tangkijvanich, P., Jantaradsamee, P., Theamboonlers, A. & Poovorawan, Y. Simultaneous quantitation and genotyping of hepatitis B virus by real-time PCR and melting curve analysis. J Virol Methods 120, 131-140, doi:10.1016/j.jviromet.2004.04.012 (2004)). Amplification refractory mutation system (ARMS) based on that oligonucleotides with a mismatched 3'-residue to the template does not efficiently extend PCR strand (Newton, C. R. et al. Analysis of any point mutation in DNA. The amplification refractory mutation system (ARMS). Nucleic Acids Research 17, 2503-2516, doi:10.1093/nar/17.7.2503 (1989)). ARMS needs only the primer to be designed with either 3'-matched or -mismatched end, and does not require neither isotopes, restriction enzymes, sequence reactions, nor specialized machines. The specificity for ARMS primers depends upon the sequence of the template (Huang, M.-M., Arnheim, N. & Goodman, M. F. Extension of base mispairs by Taq DNA polymerase: implications for single nucleotide discrimination in PCR. Nucleic Acids Research 20, 4567-4573, doi:10.1093/nar/20.17.4567 (1992)), so some modification with additional mismatches upstream to the 3' end improved the specificity without reducing its simplicity. Quenching, which is defined to decreases the fluorescence intensity of a given fluorophore, is taken advantage of signal detection in various PCR-based SNP assays (Gibson, N. J. The use of real-time PCR methods in DNA sequence variation analysis. Clin Chim Acta 363, 32-47, doi:10.1016/j.cccn.2005.06.022 (2006)).

Taq-Man quantitative PCR was applied to detect DNA sequence variance in combination with a sequence-specific probe (Holland, P. M., Abramson, R. D., Watson, R. &

Gelfand, D. H. Detection of specific polymerase chain reaction product by utilizing the 5'->3' exonuclease activity of *Thermus aquaticus* DNA polymerase. Proceedings of the National Academy of Sciences 88, 7276, doi:10.1073/pnas.88.16.7276 (1991)). The oligonucleotide probe which possesses both a fluorophore and a quencher at the different end and exhibits little fluorescence in aqueous phase are digested by the activity of 5' exonuclease in TaqMan Polymerase in the extension process of PCR, resulted in emitting the fluorescence from the dissociated fluorophore. Multiplex detection of several kinds of mutations is feasible in a single reaction tube by using different fluorophores (Nurmi, J., Ylikoski, A., Soukka, T., Karp, M. & Lovgren, T. A new label technology for the detection of specific polymerase chain reaction products in a closed tube. Nucleic acids research 28, e28-00 (2000)). In order to detect a quite rare variant, an array of modifications has been applied to the combination method with primers and probes, such as CataCleave (Harvey, J. J. et al. Characterization and applications of CataCleave probe in real-time detection assays. Anal Biochem 333, 246-255, doi:10.1016/j.ab.2004.05.037 (2004)), Scorpion-ARMS (Whitcombe, D., Theaker, J., Guy, S. P., Brown, T. & Little, S. Detection of PCR products using self-probing amplicons and fluorescence. Nature Biotechnology 17, 804-807, doi:10.1038/11751 (1999)), and peptide nucleic acid-locked nucleic acid polymerase chain reaction (PNA-LNA PCR) clamp (Zhang, S. et al. Ultrasensitive and quantitative detection of EGFR mutations in plasma samples from patients with non-small-cell lung cancer using a dual PNA clamping-mediated LNA-PNA PCR clamp. Analyst 144, 1718-1724 (2019)), whose sensitivity represent 5%, 1%, and 1%, respectively. A double strand DNA fragment has an inherent melting temperature, which is applied to a probe-based fluorescence melting curve analysis. Using a probe with a fluorophore and a quencher at the different end, the minus differentiating signal with temperature of a probe-template hybrid are plotted in the relation with temperature, resulted in the discriminated peak depended upon the sequence even in a single nucleotide called as fluorescence melting curve analysis (Huang, Q. et al. Multiplex fluorescence melting curve analysis for mutation detection with dual-labeled, self-quenched probes. PLoS One 6, e19206, doi:10.1371/journal.pone.0019206 (2011)). Although the above-mentioned methodologies have improved the specificity and sensitivity, the single cell biology required the development of a single cell-based technology. Third generation of PCR, digital PCR that is based on microwell chip, water-in-oil, and microfluidic techniques, emerged to detect one target sequence with an analytic system based on Poisson distribution (Huggett, J. F. et al. The Digital MIQE Guidelines: Minimum Information for Publication of Quantitative Digital PCR Experiments. Clinical Chemistry 59, 892, doi:10.1373/clinchem.2013.206375 (2013)). The droplet digital PCR (ddPCR) using the water-in-oil droplet technique exhibited higher sensitivity to distinguish rare mutations with 0.001% of sensitivity (Watanabe, M. et al. Ultra-Sensitive Detection of the Pretreatment EGFR T790M Mutation in Non-Small Cell Lung Cancer Patients with an EGFR-Activating Mutation Using Droplet Digital PCR. Clinical Cancer Research 21, 3552, doi:10.1158/1078-0432.CCR-14-2151 (2015)).

Digital droplet PCR is an assay based on TaqMan qPCR with microfluidic technology that enables the precise quantification for target nucleotides with high sensitivity and specificity, such as rare variant/SNP detection (Mazaika, E., and Homsy, J. (2014). Digital Droplet PCR: CNV Analysis and Other Applications. Curr Protoc Hum Genet 82, 7 24 21-13). In this invention, we introduced ddPCR as a general detection method for identifying heteroplasmy within a single cell. This analysis reveals whether the heteroplasmy based on current conventional methods is an intercellular heteroplasmy in which each cell has a homoplasmic mtDNA that is different from each other, termed macro-heteroplasmy, or an intracellular heteroplasmy in which each cell has different kinds of mtDNA, termed micro-heteroplasmy (Aryaman, J., Johnston, I. G. & Jones, N. S. Mitochondrial Heterogeneity. Front Genet 9, 718, doi:10.3389/fgene.2018.00718 (2018)).

As provided herein, the detection system can be used for detecting or monitoring the presence of heteroplasmy, either intracellularly, intercellularly, or both. This has applications for use in diagnosing a mitochondrial related disease or disorder, as well as monitoring the efficacy of a mitochondrial replacement therapy in a patient having or suspected of having heteroplasmy. In addition, the detection system can be used in a method of identifying a threshold level of heteroplasmy for use in stratifying a patient population as likely to be responsive to treatment with a mitochondrial replaced cell (MirC).

Detecting heteroplasmy at a single cell level allows for identifying cells that have homogenous intercellular mtDNA, as well as single cells that have heterogeneous intercellular mtDNA. In addition, comparison of the plurality of single cell mtDNA sequences enables identification of heterogeneous intracellular mtDNA. In addition, as described above, it can allow for the identification of a threshold level of heteroplasmy that results in a phenotype of a mitochondrial disease or disease, and/or stratifying a patient population as likely to be responsive to treatment with a mitochondrial replaced cell (MirC).

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

8. EXAMPLES

Example I

Single-Cell Digital Droplet PCR

This example demonstrates a method to evaluate the heteroplasmy of mtDNA in a single cell in the presence or absence of the mutated mtDNA that doesn't require laser capture or other sorting assays.

Normal human dermal fibroblasts (NHDF) were obtained from Lonza (Walkersville, Md., USA). Mitochondrial disease patient-derived skin fibroblasts (BK01/02/04) were kindly provided by non-profit organization (NPO) Koinobori that supports the research for mitochondrial diseases under the approval of both Department of Regenerative Medicine, Kyoto Prefectural University of Medicine, Kyoto, Japan and Koinobori's ethical committees. The clinical characteristics of these primary cells were summarized in Table 1.

TABLE 1

| Code# | Disease | Mutation | Age at harvest | Sex | Relation to Proband |
|---|---|---|---|---|---|
| BK01 | MELAS | mtDNA A3243G (mt-tRNA) | 30 | M | Y |
| BK02 | Leigh Syndrome | mtDNA T10158C (Complex 1 MT-ND3) | 6 | F | N |
| BK04 | Leigh Syndrome | mtDNA T9185C (Complex V MT-ATP6) | 1 | F | Unknown |

The NHDF were maintained in Dulbecco's Modified Eagle's Medium (Thermo Fisher Scientific, Waltham, Mass., USA) supplemented with 10% fetal bovine serum (Thermo Fisher Scientific), 1% penicillin/streptomycin. BK01 were cultured in FBM™ Fibroblast Basal Medium supplemented with FGM™-2 SingleQuots™ (hFGF-B, insulin, FBS and gentamicin/amphotericin-B) (LONZA). BK02 and BK04 were cultured in Dulbecco's Modified Eagle's Medium low glucose (Thermo Fisher Scientific) supplemented with 10% fetal bovine serum (Thermo Fisher Scientific) and 1% penicillin/streptomycin. All cells were incubated at 37° C. in a humidified 5% CO2 incubator.

Cells were trypsinized, suspended in culture medium, then centrifuged (1000 rpm, 5 min) to pellet, and resuspended in PBS. The resuspended cells were added into 4% Paraformaldehyde (FUJIFILM Wako Pure Chemical Corporation, Osaka, Japan) and fixed for at least 15 min at Room temperature. After fixed, the cells were centrifuged (1500 rpm, 5 min), resuspended in Propidium iodide solution composed of 50 µg/ml Propidium iodide, 0.1 mg/ml RNaseA, 0.05% TritonX-100 and PBS, and incubated for 40 min at 37° C. After washed with PBS, pelleted (1500 rpm, 5 min), and responded with PBS. The samples were immediately analyzed by flow cytometry. Cell cycle phase distribution was determined using Flowjo software.

Heteroplasmy of mitochondrial DNA was determined by TaqMan SNP genotyping assay. Wild-type and mutant allele-specific TaqMan proves and primers were designed and produced by Thermo Fisher Scientific. The two probes were labeled with different fluorophores (FAM and VIC), and attached a quencher at another end. The genomic DNA was extracted from cells by using NucleoSpin® Tissue (TAKARA Bio, Tokyo, Japan). The extracted genomic DNA (100 ng) was used for quantitative PCR mixed with the forward and reverse primers, the probes, and the TaqMan Genotyping Master Mix (Thermo Fisher Scientific) on a CFX connect real-time system (BioRad) under the following conditions: 40 cycles of PCR (95° C. for 15 sec. and 60° C. for 1 min.) after initial denaturation (95° C. for 10 min.). A calibration curve was created by above-mentioned quantitative PCR using plasmid of decided copy numbers containing the amplified targeted mtDNA fragments for either wild-type or mutant sequences. The primers used in this experiment are listed in FIG. 1.

The sc-ddPCR system commenced with the encapsulation of a single cell into one oil droplet and then proceeded to the step of PCR with a set of the primers and the fluorescent probes using TaqMan polymerase with 5' to 3' exonuclease, which releases the fluorophore from the probe, followed by detection of the fluorescent signal in the droplets. The PCR reaction mixture consisted of: 4 µl resuspended cells at a concentration of $1.25 \times 10^5$ cells/ml, 10 µl 2×ddPCR supermix (Bio-Rad); wild-type and mutant allele-specific TaqMan probes at a concentration of 0.25 µM; primer mixtures at a concentration of 0.9 µM for the target gene, and nuclease-free water added up to 20 µl. Droplets were generated using the Bio-Rad QX200 system (Bio-Rad) following the manufacturer's instructions. The reactions were transferred to a 96-well plate (Eppendorf, Hamburg, Germany) for the PCR reactions using a Thermal Cycler (Bio-Rad) under the following conditions: amplification was carried out on a regular ramp rate of 2.0° C./sec, at 95° C. for 10 min followed by 40 cycles of 30 sec at 94° C. plus 1 min at 53° C. The final enzyme deactivation step occurred at 98° C. for 10 min. The 96-well plate was transferred to a QX200 Droplet Reader (Bio-Rad) and analyzed for the number of fluorescent-positive droplets. Each droplet was analyzed individually using a two-color detection system (set to detect FAM and VIC). The fluorescent droplets are counted to provide absolute quantification of target mtDNA in digital form using QuantaSoft software (Bio-Rad). We added various numbers of targeted cells to the PCR reaction mix and generated droplets in order to ensure single-cell encapsulation. The 500 cells per a sample were successfully encapsulated into droplets and single-cell encapsulation was observed.

Three kinds of cells derived from patients suffered from mitochondrial diseases were examined in this study. The characteristics of these cells were summarized in Table 1. These primary fibroblasts were isolated from the skin biopsies of patients, established as cultured cells based on the acceptance of the ethical committee in Koinobori Associate Inc that is a NPO for mitochondrial diseases in Japan, and gifted for the research under the acceptance of the institutional ethical committee in Kyoto Prefectural University of Medicine. BK01 was derived from a female patient at the age of 30 for mitochondrial myopathy, encephalopathy, lactic acidosis, and stroke-like episodes (MELAS) whose culprit is the mutation of A to G in m3243 in tRNA for leucin. The other two fibroblasts were generated from female patients with Leigh syndrome in 6 and 1 years old. One of the Leigh syndrome cell lines harbored the mutation of T to C in m10158, which is located in mitochondrially encoded NADH dehydrogenase 3 (MT-ND3) that is part of the respiratory chain Complex I, also known as NADH dehydrogenase (ubiquinone), which consists of 37 nuclear and 7 mitochondrially encoded subunits. The other Leigh syndrome cell line has the mutation of T to C in m9185 that is located in mitochondrially encoded ATP synthase membrane subunit 6, which encodes the ATP synthase $F_O$ subunit 6 (MT-ATP6) that is the subunit of the F, 1F0 ATPase, also known as Complex V, which consists of 14 nuclear and 2 mitochondrial encoded subunits. The proband in BK01 was identified in her mothers, and the mutation of BK02 was de novo. The inheritance of BK04 was not determined.

Figure 1:
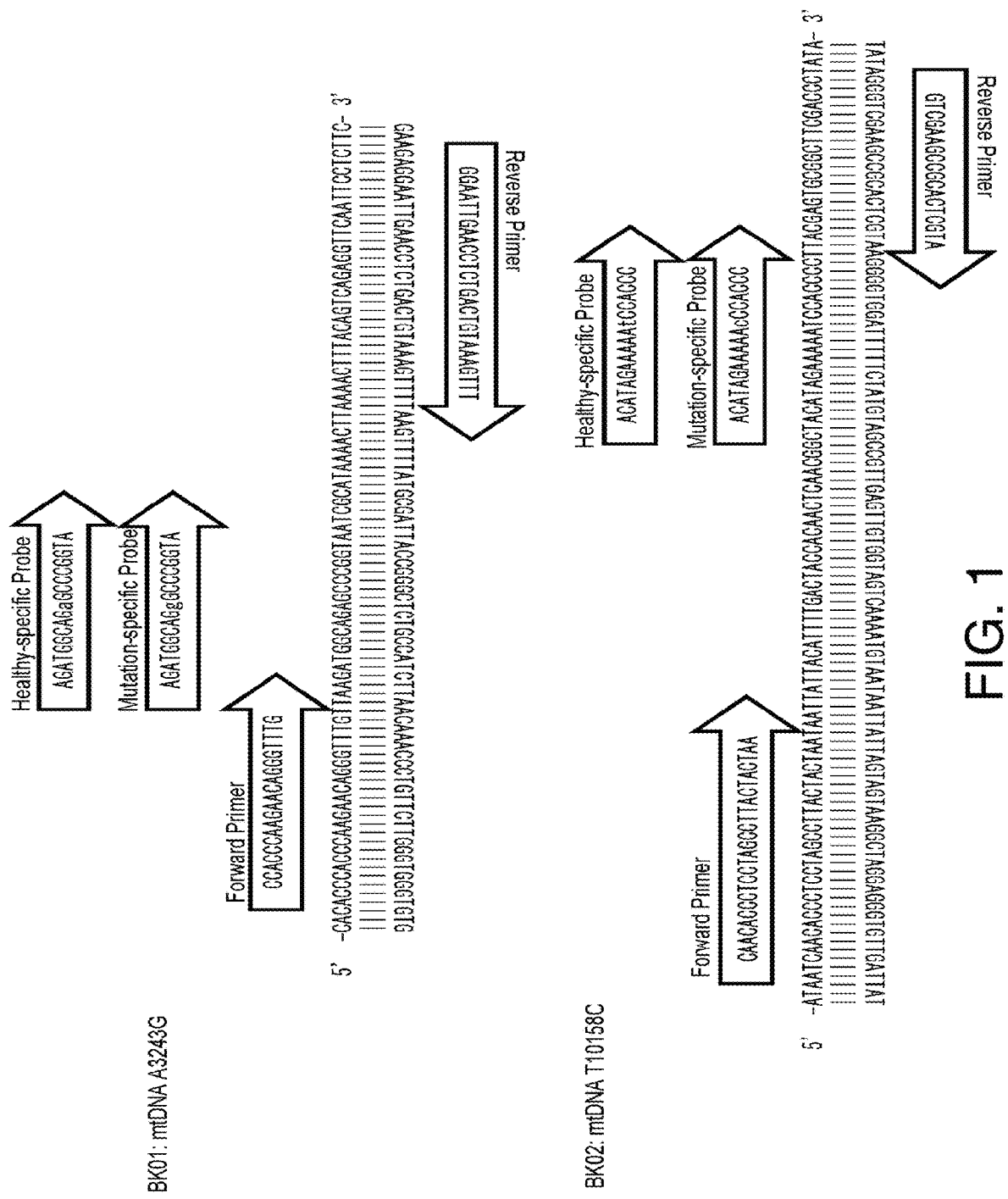
FIG. 1 illustrates the strategy used for heteroplasmy analysis for fibroblasts from patients with primary mitochondrial diseases (BK01, BK02, and BK04) bearing a single mitochondrial DNA mutation and the design of the primers used for the SNP genotyping assay. SEQ ID NOs: 1-15 are depicted.
Figure 1:
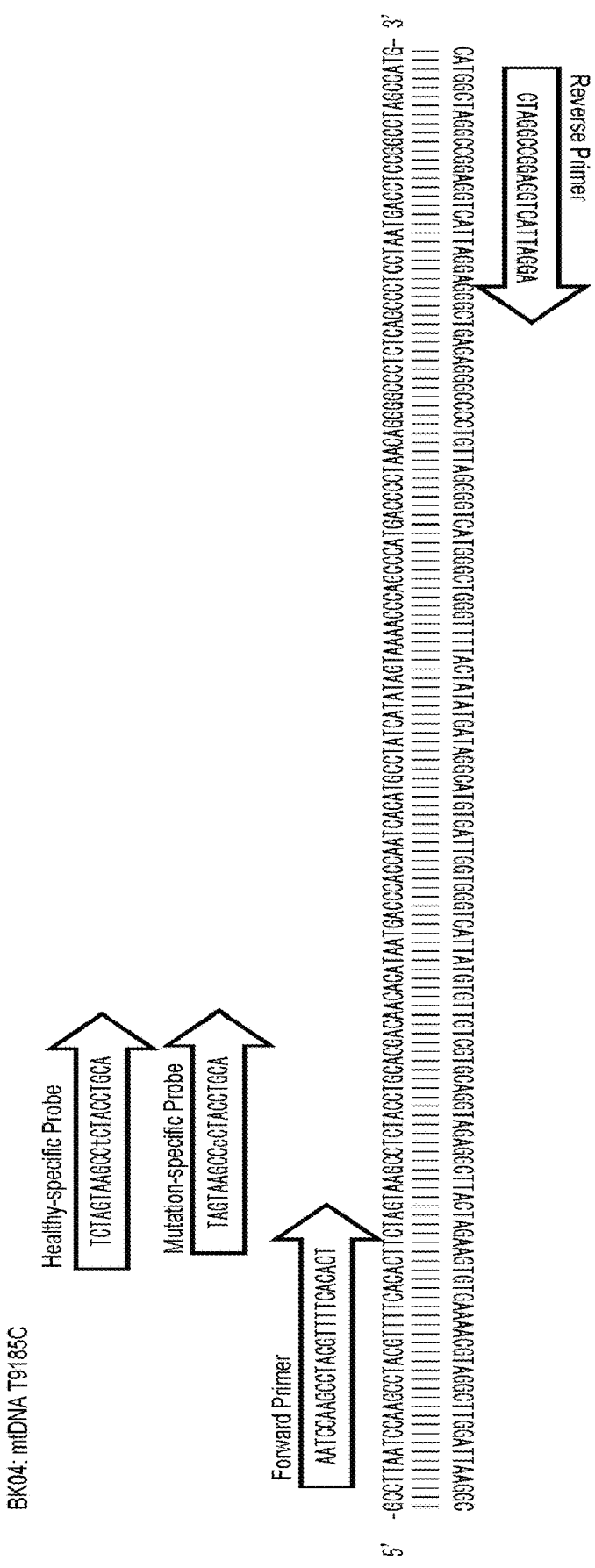
Figure 2:
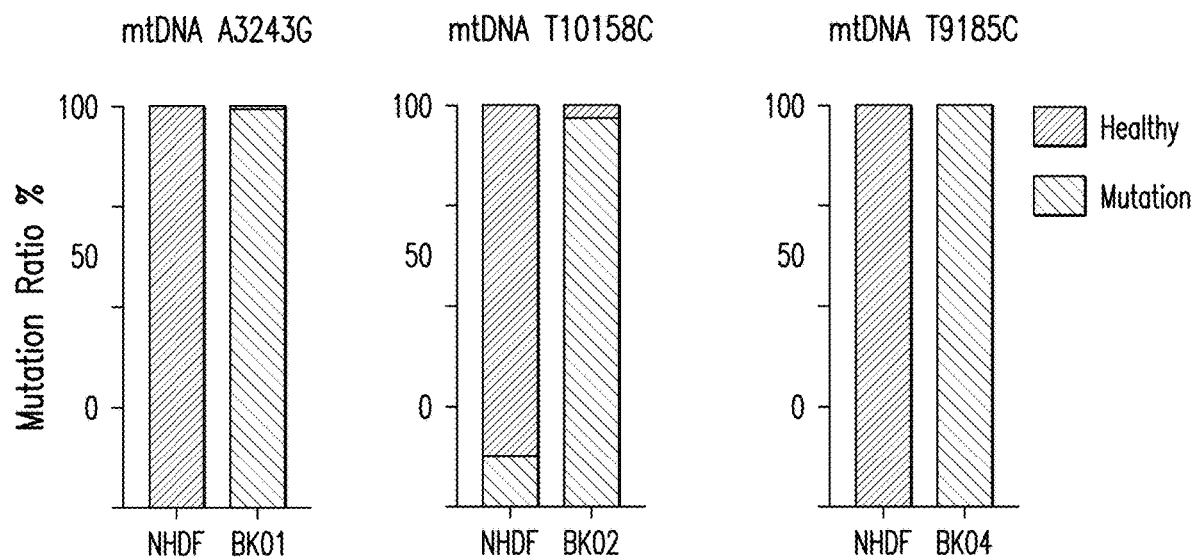
FIG. 2 illustrates that the gross heteroplasmy of three fibroblasts from patients with primary mitochondrial diseases was 99.8%, 96.9%, and 99.7% for BK01, BK02, and BK04, respectively.

TaqMan single nucleotide polymorphism (SNP) assay was chosen to determine the heteroplasmy in mtDNA of target cells with respect to the simplicity, because the same assay is easily adopted to ddPCR. A set of primers was designed to target the SNP-encompassing region and amplify 83 bp, 100 bp, and 151 bp sequence for BK01, BK02, and BK04, respectively. To discriminate and quantify healthy genotype compatible to Cambridge Reference Sequence (CRS) and the mutated mtDNA separately, two TaqMan proves with either FAM or VIC fluorescent dye at 5'-end and non-fluorescent quencher at 3'-end were designated in combination with minor groove-binding (MGB) to maximize the difference of the melting temperature in each kind of fibroblasts. The amplified sequences were subcloned into a plasmid to depict the standard line for quantification of the target sequence (FIG. 1). The gross heteroplasmy of three fibroblasts were 99.8%, 96.9%, and 99.7% for BK01, BK02, and BK04, respectively (FIG. 2).

TABLE 2

| Mutation site | Cell name | Healthy ratio % | Mutation ratio % |
| --- | --- | --- | --- |
| mtDNA A3243G | NHDF | 100 | 0 |
| | BKO1 | 0.2 | 99.8 |
| mtDNA T10158C | NHDF | 87.3 | 12.7 |
| | BK02 | 3.1 | 96.9 |
| mtDNA T9185C | NHDF | 100 | 0 |
| | BK04 | 0.3 | 99.7 |

Figure 3:
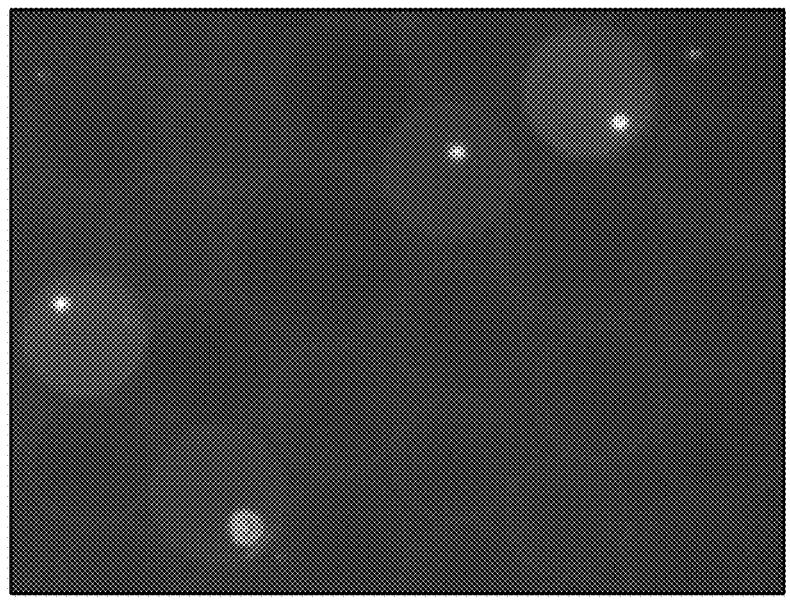
FIG. 3 illustrates that a concentration of $1\times10^5$ cells per milliliter was an optimal dilution to achieve a cell suspension to enable ddPCR in a single cell level.
Figure 4:
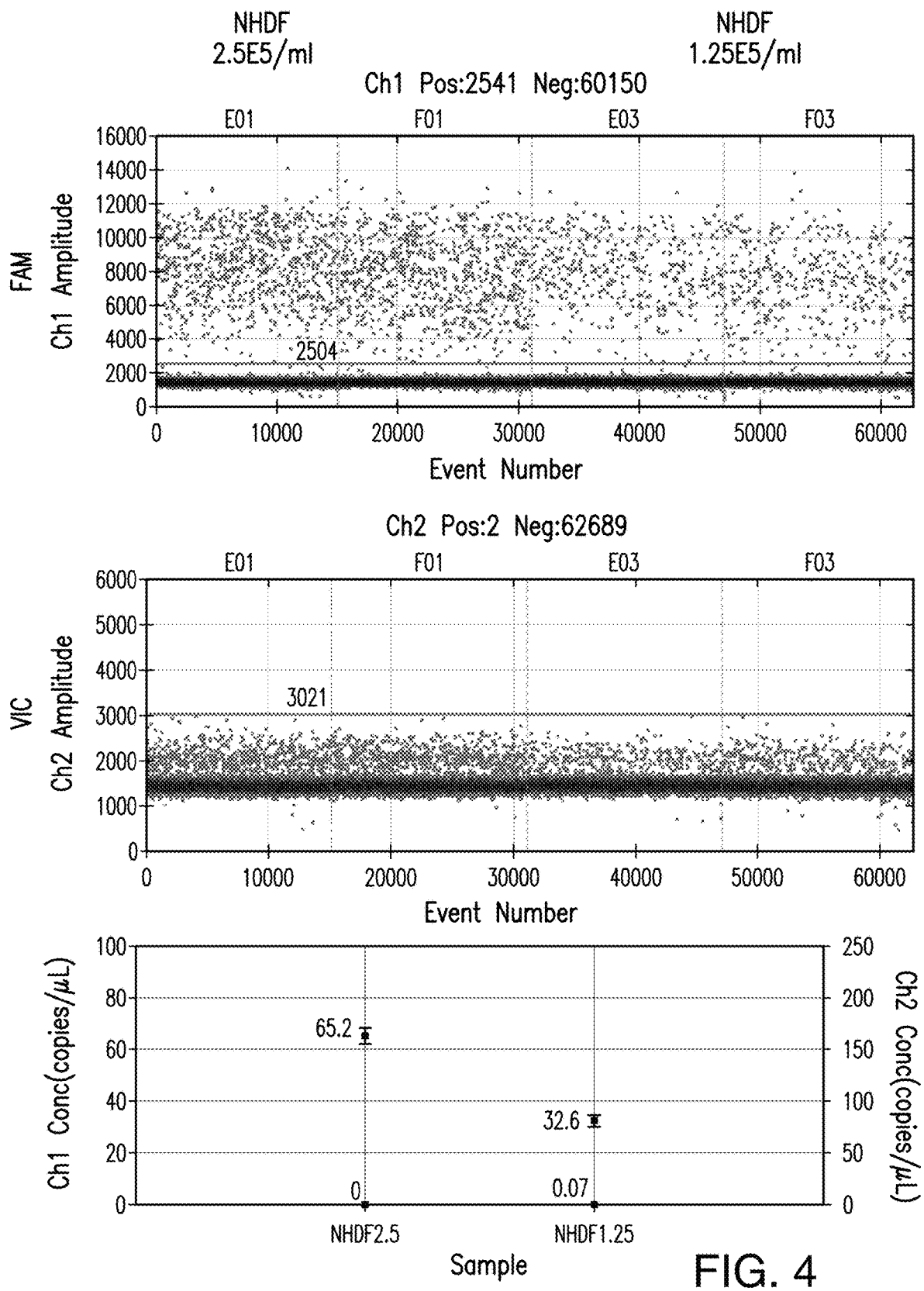
FIG. 4 illustrates achievement of the threshold line, based on the proportional relation between the cell number of the positive signal and the loaded cell number.
Figure 4:
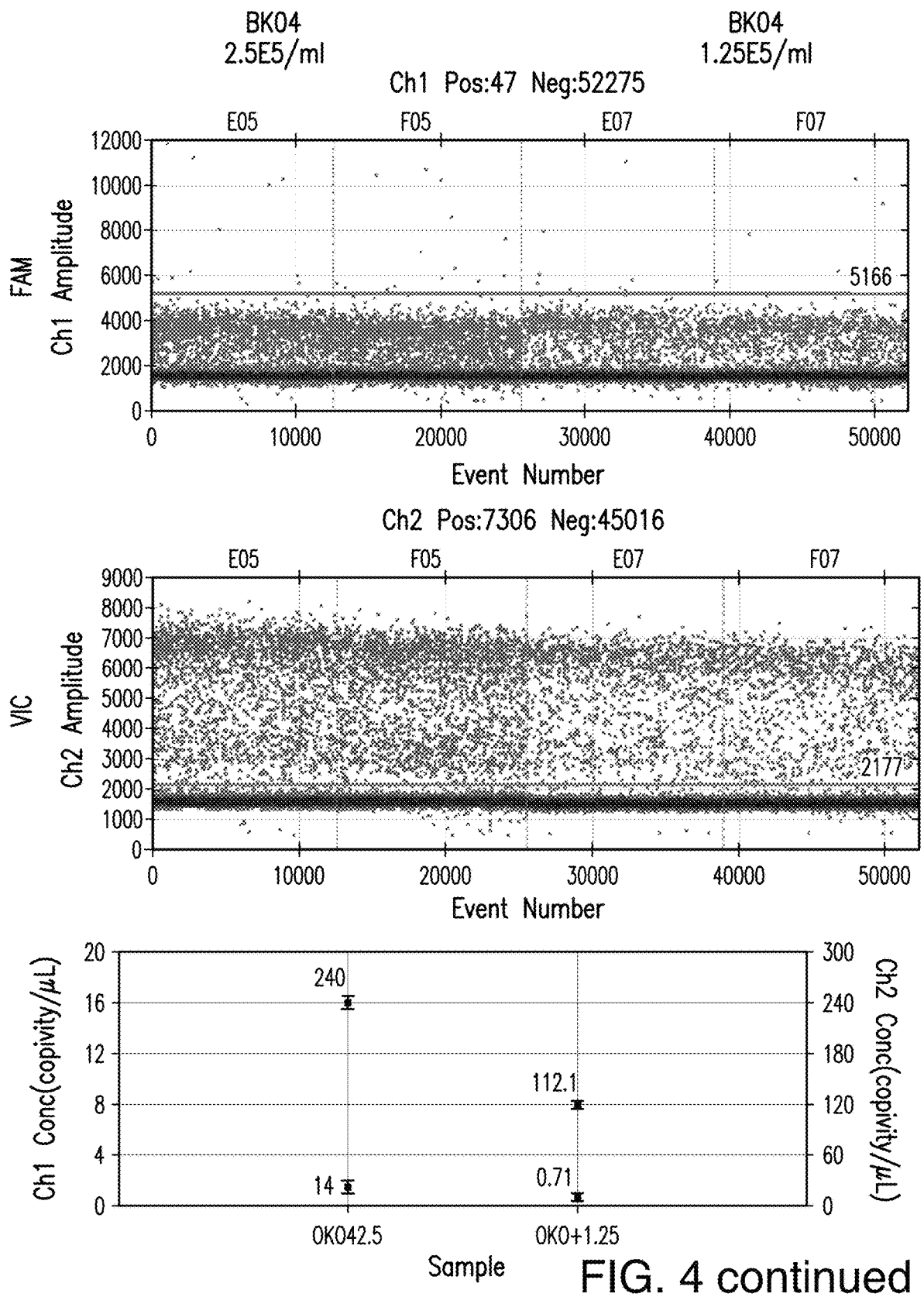

Droplets were generated by using various concentration of the cell suspension so that they include either a single cell or no cell. The concentration of 1×10⁵ cells per milliliter was optimal (FIG. 3). Normal human dermal fibroblasts (NHDF), which were sequenced for mtDNA and ensured to have compatible sequence to CRS in MT-ND3, MT-ATP6, and tRNA for leucin, were utilized as the control. All three kinds of the primer set and the probe sets for mutations in m3243, m10158, and m9185 were designed, based on the predicted melting temperature between the probe and the template. The PCR reaction was optimized to include 40 cycles of PCR (94° C. for 30 sec and 56° C. for 2 min.) with final heating (98° C. for 10 min) after initial denaturation (95° C. for 10 min). Following the optimization of PCR reaction, the threshold line was sat, based on the proportional relation between the cell number of the positive signal and the loaded cell number (FIG. 4).

We depicted the results as a quadrant format with a healthy signal as Y-axis and a mutant signal as X-signal. The quadrant analysis shows cells possessing only mutant mtDNAs in lower right quadrant, cells possessing both mutant and healthy mtDNAs d in upper left quadrant, cells possessing only healthy mtDNA in upper left. The lower left quadrant exhibits droplets without a cell (FIG. 5). The quadrant analysis in BK01 showed that a major part of cells, 95.56%, was homoplasmy in the mutant mtDNA plotted in lower left, but a minor part of cells had two kinds of mtDNA, the mutant and the healthy, plotted in upper right, which is the state of an intracellular heteroplasmy (FIG. 5 Upper panel). Moreover, a population of cells constituted from sole healthy mtDNA existed at the same rate, 1.72%, as the cells with an intracellular heteroplasmy. BK02 contained the cell population with both the mutant and the healthy mtDNA plotted in upper right at the rate of 4.76% (FIG. 5 Middle panel). BK04 showed the difference from the others in respect that there is only a single fraction of cells with sole mutated mtDNA (FIG. 5 Lower panel). Both BK02 and BK04 did not contain a cell population with only the healthy mtDNA.

In quadrant analysis, there were two distinct fractions in left upper or right lower quadrant, although it was difficult to judge whether two populations were in right upper quadrant due to small events. Cell cycle analysis revealed that the fractions of S phase in three cell lines derived from patients with mitochondrial disease were less than half, compared with that in NHDF. The sum of G2/M and S phase were ranged from 10 to 20% in diseased fibroblasts (FIG. 6). The ratios of two fractions were nearly even, suggesting that the duplicated content of mtDNA might occupy the half of the cell cycle.

This study provides a method to evaluate the heteroplasmy of mtDNA in a single cell in the presence or an absence of the mutated mtDNA. Since the conventional methods for the heteroplasmy in mitochondrial diseases have uniformly target a group of cells, such as mononuclear cells and biopsied skeletal muscle, the outputs have not been able to discriminate an intracellular (micro-heteroplasmy) and an intercellular heteroplasmy (macro-heteroplasmy). Although the threshold theory that mitochondrial diseases phenotypically come up when the heteroplasmy of mutated mtDNA reaches over 60 to 70% is based on clinical samples, it's unclear which is the case, that all cells have a similar heteroplasmy, or that cells with homoplamsy with either healthy or mutated mtDNA are mixed at the heteroplasmy rate, or that the former and the latter are mixed. Moreover, whether the threshold theory is justified at the single cell level remain to be examined.

Further single cell biology with respect of the heteroplasmy in mtDNA shed the light on the avenue to better understandings of not only mitochondrial diseases, but also neurodegenerative diseases, cancers, and aging.

Example II

Analysis of the Heteroplasmy in Mitochondria Replaced T Cells (MirT) Using Single Cell Digital Droplet qPCR This example demonstrates a method to analyze heteroplasmy in mitochondria replaced T cells (MirT) using single cell digital droplet qPCR.

Human peripheral blood was drawn from a healthy volunteer, and separated into mononuclear fraction by using Ficoll density gradient method. Human primary T cells (hereafter named as G-T cells) were expanded under the presence of IL-7 and IL-15 at the concentration of 20 μg/ml and 10 μg/ml, respectively, onto anti-CD3 and anti-CD28 antibody coated plates. Mitochondrial replaced T cells were generated with donor mitochondria derived from EPC100.

The sequence of hyper variable region 1 (HVR1) in mitochondrial DNA (mtDNA) (FIG. 7) were examined to discriminate two kinds of mtDNA. The positions of mtDNA124 and mtDNA130 were C and C in G-T cells, whereas T and T in EPC100 (FIG. 8). Taking advantage of these differences, the probes specific for G-T cells and EPC100 in TaqMan qPCR single nucleotide polymorphism (SNP) genotyping assay were designed to encompass these points, CAAcCAACCcTCAAC (SEQ ID NO: 18) with fluorescent FAM and AGCAAtCAACCtTCAAC (SEQ ID NO: 19) with fluorescent VIC, respectively (FIG. 9). The small characters in the sequences express the difference between the two kinds of cells. And, the primer set including the probe region was also designed. Two recombinant plasmids carrying a PCR fragment specific for G-T cells or EPC100 were created and provided a standard curve for the quantification of mtDNA copy number by TaqMan qPCR.

MirT cells were generated according to the following protocol: on day0, G-T cells were transferred with mRNA coding XbaIR by electroporation (ATX, MaxCyte Inc.). G-T cells, whose mitochondrial DNA was significantly reduced, called ρ(−) cells, were maintained in the modified conditions of the initial expansion culture by the addition of uridine and pyruvate for one week. Donor isolated mitochondria were co-cultured with the ρ(−) G-T cells in the expansion culture condition. TaqMan qPCR SNP genotyping assays for the whole cells were carried out on day 9 and day 14, meaning 2 days and 7 days following mitochondria transfer, whereas single cell digital droplet PCR (sc-ddPCR) was executed on day 14, meaning 7 days after mitochondrial transfer (FIG. 10).

For the whole population, SNP assays (FIG. 11) were performed by PCR of the hmtDNA D-loop (hmtD loop-F:

ctctgttctttcatgggggaagc (SEQ ID NO: 22); hmtHV1-R: atc-catggggacgagaaggga (SEQ ID NO: 23)) using the following conditions:

| 181027 PCR | human_G_T cell | x8 | EPC 100 mt DsRed | x8 |
|---|---|---|---|---|
| 10x HIFI Buffer | 2.5 | 20 | 2.5 | 20 |
| 10 mM dNTPs | 0.1 | 0.8 | 0.1 | 0.8 |
| 50 mM MgSO4 | 1 | 8 | 1 | 8 |
| Primer mix (1/10) | 1 | 8 | 1 | 8 |
| gDNA (80 ng) | 0.42 | 3.4 | 0.20 | 1.6 |
| Platinum Taq | 0.1 | 0.8 | 0.1 | 0.8 |
| DW | 19.9 | 159.0 | 20.1 | 160.8 |
| | 25 | 200 | 25 | 200 |

After initial denaturation (94° C. for 2 min), the PCR reaction included 35 cycles of PCR (94° C. for 30 sec, 59° C. for 30 sec, and 68° C. for 1 min) with a final extension at 68° C. for 2 min). The results demonstrated that the exogenous mtDNA occupied a half in 2 days, and about 70% in 7 days following the transfer, respectively (FIG. 12). For sc-ddPCR, SNP assays demonstrated the compatible rate in endogenous and exogenous mtDNA to the whole population SNP assays, which verified the robustness for sc-ddPCR analysis (FIG. 13).

Importantly, quadrant analysis indicated that almost all cells were homoplasmy with either endogenous or exogenous mtDNA, but there are few cells with intracellular heteroplasmy or micro-heteroplasmy. Our results of sc-ddPCR clearly demonstrated that mitochondria replaced cells (MirC) could produce a near complete replacement of the mtDNA a single cell level.

Taken together, these results demonstrate that identification of the mtDNA content at a single cell level can be used to identify MirC with nearly a complete replacement of mtDNA. Application of this technology can be used for not only T cells, but also stem cells, which could provide an eradicative for mitochondrial diseases, for which palliative treatment only exist in current medicine.

Example III

Application of Sc-ddPCR in Patient-Derived Peripheral Blood

This example demonstrates a method to analyze heteroplasmy in MELAS cells using sc-ddPCR and FACS analysis.

Peripheral blood obtained from a 23 year old female MELAS patient carrying mitochondrial A3243G mutation and an healthy donor (labeled as GJ) was examined by a single cell ddPCR protocol. Following isolation of mononuclear cells by a density gradient centrifugation, the cells were further sorted for CD3+ cells or CD11b+ cells, which are surface markers for T cells and macrophage-monocyte lineages, respectively.

The conventional single nucleotide polymorphism (SNP) genotyping assay using TaqMan polymerase was applied to the whole cells population, which was split into 3 samples. Heteroplasmy of A3243G mutation in MELAS patient-derived mononuclear cells was 27%, whereas the A3243G levels in the healthy control were negligible (FIG. 14).

Next, the sorted lineage cells and whole mononuclear cells were split into four samples for sc-ddPCR to prevent biased results. To gain better visibility of results in sc-ddPCR, digital data were imported into FlowJo, which is an application software for a standard FACS machine. The results were displayed as a quadrant contour plot with x-axis of mutant sequence and y-axis of healthy sequence following an adequate compensation (see, e.g., FIGS. 15-18).

The control sample showed negligible A3243G heteroplasmy without variabilities between the samples, which is consistent with the conventional SNP genotyping assay (see, e.g., FIG. 15). The MELAS patient' derived blood samples demonstrated that cells with mutant A3243G homoplasmy, healthy homoplasmy, and intracellular A3243G heteroplasmy were about 18.4%, 72.4%, and 9.1%, respectively, for the whole mononuclear population (see, e.g., FIG. 16). T cells in MELAS patient exhibited a lower rate in mutant A3243G homoplasmy (about 6.9%) and a higher rate of healthy homoplasmy (about 88.2%) than those in the whole population (see, e.g., FIG. 17). Cells with the intracellular A3243G heteroplasmy in T cells of the MELAS patient were rare (see, e.g., FIG. 17). On other hand, macrophage-monocyte lineage cells showed higher in mutant A3243G homoplasmy (about 25%) and lower rate of healthy homoplasmy (about 62.4%) than those in the whole mononuclear population (see, e.g., FIG. 18). The intracellular heteroplasmy was much higher in the macrophage-monocyte lineage than the whole population and T cells (see, e.g., FIG. 18).

These results showed there is a difference mutant A3243G expression between lineages in respect of intercellular A3243G heteroplasmy. Cells with mutant A3243G homoplasmy dominated in each lineage, compared with intracellular A3243G heteroplasmy, suggesting an unstability of the intracellular A3243G heteroplasmy, in contrast of a stability of the homoplasmy (FIG. 19).

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method for treating a subject having a mitochondrial disease or disorder associated with high rates of a pathogenic mitochondrial DNA (mtDNA) mutation, comprising:
   (a) administering to the subject a first therapy that affects mtDNA
   (b) obtaining a biological sample comprising a plurality of single cells from the subject after administration of the first therapy;
   (c) determining a level of mtDNA heteroplasmy in the biological sample, comprising:
      (i) encapsulating each cell of the plurality of single cells into a single droplet and performing single cell digital droplet PCR to detect wild-type and mutant intracellular mtDNA in each of the plurality of single cells in a single assay;
      (ii) determining a proportion of wild-type and mutant intracellular mtDNA sequences within each of the plurality of single cells; and
      (iii) calculating an amount of intercellular variability in the intracellular mtDNA sequences between each of the plurality of single cells, and calculating an amount of intracellular variability in the intracellular mtDNA sequences within each of the plurality of single cells;
   (d) determining whether the level of mtDNA heteroplasmy in the biological sample is below a threshold level of mtDNA heteroplasmy that mainifests in the mitochondrial disease or disorder; and
   (e) further administering to the subject a second therapy that affects mtDNA if the mtDNA heteroplasmy level is not below the threshold level of mtDNA heteroplasmy that manifests in the mitochondrial disease or disorder.

2. The method of claim 1, wherein the first therapy, the second therapy, or both comprises a cell therapy.

3. The method of claim 1, wherein the first therapy, the second therapy, or both comprises a mitochondrial replacement therapy.

4. The method of claim 1, wherein the first therapy, the second therapy, or both comprises mitochondrial replaced cells (MirCs).

5. The method of claim 1, wherein the subject is a human.

6. A method for monitoring the efficacy of a therapy that affects mitochondrial DNA (mtDNA) in a subject having a mitochondrial disease or disorder associated with rates of a pathogenic mtDNA mutation above a threshold level of mtDNA heteroplasmy that manifests in the mitochondrial disease or disorder, comprising:
   (a) administering the therapy to the subject;
   (b) obtaining a biological sample comprising a plurality of single cells from the subject after administration of the therapy;
   (c) determining a level of mtDNA heteroplasmy in the biological sample, comprising:
      (i) encapsulating each cell of the plurality of single cells into a single droplet and performing single cell digital droplet PCR to detect wild-type and mutant intracellular mtDNA in each of the plurality of single cells in a single assay;
      (ii) determining a proportion of wild-type and mutant intracellular mtDNA sequences within each of the plurality of single cells; and
      (iii) calculating an amount of intercellular variability in the intracellular mtDNA sequences between each of the plurality of single cells, and calculating an amount of intracellular variability in the intracellular mtDNA sequences within each of the plurality of single cells;
   (d) determining whether the level of mtDNA heteroplasmy in the biological sample is below a threshold level of mtDNA heteroplasmy that mainifests in the mitochondrial disease or disorder; and
   (e) further administering to the subject if the mtDNA heteroplasmy level is not below the threshold level of mtDNA heteroplasmy that manifests in the mitochondrial disease or disorder.

7. The method of claim 6, wherein the subject is human.

8. The method of claim 6, wherein the therapy that affects mtDNA comprises a cell therapy.

9. The method of claim 6, wherein the therapy that affects mtDNA comprises a mitochondrial replacement therapy.

10. The method of claim 6, wherein the therapy that affects mtDNA comprises mitochondrial replaced cells (MirCs).

11. The method of claim 1, wherein the threshold level of mtDNA heteroplasmy that manifests in the mitochondrial disease or disorder has been identified by a method comprising the following steps:
    (a) obtaining a biological sample comprising one or more single cells from a subject that manifests in the mitochondrial disease or disorder;
    (b) determining a level of mtDNA heteroplasmy in the biological sample, comprising:
       (i) encapsulating each cell of the plurality of single cells into a single droplet and performing single cell digital droplet PCR to detect wild-type and mutant intracellular mtDNA in each of the plurality of single cells in a single assay; and
       (ii) determining a proportion of wild-type and mutant intracellular mtDNA sequences within each of the plurality of single cells;
       (iii) calculating an amount of intercellular variability in the intracellular mtDNA sequences between each of the plurality of single cells, and calculating an amount of intracellular variability in the intracellular mtDNA sequences within each of the plurality of single cells; and
    (c) identifying the minimum level of heteroplasmy that specifically correlates with the mitochondrial disease or disorder, thereby determining said threshold level of heteroplasmy that manifests in said mitochondrial related disease or disorder.

12. The method of claim 1, wherein the first therapy and the second therapy are the same.

13. The method of claim 1, wherein obtaining the biological sample does not comprise laser capture.

14. The method of claim 6, wherein obtaining the biological sample does not comprise laser capture.

15. The method of claim 1, wherein the biological sample is obtained from human peripheral blood.

16. The method of claim 6, wherein the biological sample is obtained from human peripheral blood.

* * * * *

SEQUENCE LISTING

<160> NUMBER OF SEQ ID NOS: 24

<210> SEQ ID NO 1
<211> LENGTH: 18
<212> TYPE: DNA
<213> ORGANISM: Artificial Sequence
<220> FEATURE:
<223> OTHER INFORMATION: Healthy -specific Probe - BK01-mtDNAA3243G

<400> SEQUENCE: 1

```
agatggcaga gcccggta                                               18

<210> SEQ ID NO 2
<211> LENGTH: 18
<212> TYPE: DNA
<213> ORGANISM: Artificial Sequence
<220> FEATURE:
<223> OTHER INFORMATION: Mutation-specific Probe - BK01-mtDNAA3243G

<400> SEQUENCE: 2
agatggcagg gcccggta                                               18

<210> SEQ ID NO 3
<211> LENGTH: 20
<212> TYPE: DNA
<213> ORGANISM: Artificial Sequence
<220> FEATURE:
<223> OTHER INFORMATION: Forward Primer - BK01-mtDNAA3243G

<400> SEQUENCE: 3
ccacccaaga acagggtttg                                             20

<210> SEQ ID NO 4
<211> LENGTH: 27
<212> TYPE: DNA
<213> ORGANISM: Artificial Sequence
<220> FEATURE:
<223> OTHER INFORMATION: Reverse Primer - BK01-mtDNAA3243G

<400> SEQUENCE: 4
ggaattgaac ctctgactgt aaagttt                                     27

<210> SEQ ID NO 5
<211> LENGTH: 93
<212> TYPE: DNA
<213> ORGANISM: Artificial Sequence
<220> FEATURE:
<223> OTHER INFORMATION: BK01-mtDNAA3243G

<400> SEQUENCE: 5
cacacccacc caagaacagg gtttgttaag atggcagagc ccggtaatcg cataaaactt     60
aaaactttac agtcagaggt tcaattcctc ttc                                 93

<210> SEQ ID NO 6
<211> LENGTH: 18
<212> TYPE: DNA
<213> ORGANISM: Artificial Sequence
<220> FEATURE:
<223> OTHER INFORMATION: Healthy-specific Probe - BK02 - mt DNA T10158C

<400> SEQUENCE: 6
acatagaaaa atccaccc                                               18

<210> SEQ ID NO 7
<211> LENGTH: 18
<212> TYPE: DNA
<213> ORGANISM: Artificial Sequence
<220> FEATURE:
<223> OTHER INFORMATION: Mutation-specific Probe - BK02 - mt DNA T10158C

<400> SEQUENCE: 7
acatagaaaa acccaccc                                               18

<210> SEQ ID NO 8
<211> LENGTH: 26
```

```
<212> TYPE: DNA
<213> ORGANISM: Artificial Sequence
<220> FEATURE:
<223> OTHER INFORMATION: Forward Primer - BK02 - mt DNA T10158C

<400> SEQUENCE: 8
caacaccctc ctagccttac tactaa                                           26

<210> SEQ ID NO 9
<211> LENGTH: 18
<212> TYPE: DNA
<213> ORGANISM: Artificial Sequence
<220> FEATURE:
<223> OTHER INFORMATION: Reverse Primer - BK02 - mt DNA T10158C

<400> SEQUENCE: 9
gtcgaagccg cactcgta                                                    18

<210> SEQ ID NO 10
<211> LENGTH: 111
<212> TYPE: DNA
<213> ORGANISM: Artificial Sequence
<220> FEATURE:
<223> OTHER INFORMATION: BK02 - mt DNA T10158C

<400> SEQUENCE: 10
ataatcaaca ccctcctagc cttactacta ataattatta catttgact accacaactc       60 aacggctaca tagaaaaatc caccccttac gagtgcggct tcgaccctat a              111

<210> SEQ ID NO 11
<211> LENGTH: 21
<212> TYPE: DNA
<213> ORGANISM: Artificial Sequence
<220> FEATURE:
<223> OTHER INFORMATION: Healthy-specific Probe - BK04 - mtDNA T9185C

<400> SEQUENCE: 11
tctagtaagc ctctacctgc a                                                21

<210> SEQ ID NO 12
<211> LENGTH: 19
<212> TYPE: DNA
<213> ORGANISM: Artificial Sequence
<220> FEATURE:
<223> OTHER INFORMATION: Mutation-specific Probe - BK04 - mtDNA T9185C

<400> SEQUENCE: 12
tagtaagccc ctacctgca                                                   19

<210> SEQ ID NO 13
<211> LENGTH: 24
<212> TYPE: DNA
<213> ORGANISM: Artificial Sequence
<220> FEATURE:
<223> OTHER INFORMATION: Forward Primer - BK04 - mtDNA T9185C

<400> SEQUENCE: 13
aatccaagcc tacgttttca cact                                             24

<210> SEQ ID NO 14
<211> LENGTH: 21
<212> TYPE: DNA
<213> ORGANISM: Artificial Sequence
<220> FEATURE:
<223> OTHER INFORMATION: Reverse Primer - BK04: mtDNA T9185C
```

<400> SEQUENCE: 14
ctaggccgga ggtcattagg a    21

<210> SEQ ID NO 15
<211> LENGTH: 161
<212> TYPE: DNA
<213> ORGANISM: Artificial Sequence
<220> FEATURE:
<223> OTHER INFORMATION: BK04 - mtDNA T9185C

<400> SEQUENCE: 15
gccttaatcc aagcctacgt tttcacactt ctagtaagcc tctacctgca cgacaacaca    60
taatgaccca ccaatcacat gcctatcata tagtaaaacc cagcccatga cccctaacag    120
gggccctctc agccctccta atgacctccg gcctagccat g    161

<210> SEQ ID NO 16
<211> LENGTH: 103
<212> TYPE: DNA
<213> ORGANISM: Artificial Sequence
<220> FEATURE:
<223> OTHER INFORMATION: human T-cell HVR1

<400> SEQUENCE: 16
ccccccccca tgcttacaag caagtacagc aaccaaccct caactatcac acatcaactg    60
caactccaaa gccacctctc acccactagg ataccaacaa acc    103

<210> SEQ ID NO 17
<211> LENGTH: 239
<212> TYPE: DNA
<213> ORGANISM: Artificial Sequence
<220> FEATURE:
<223> OTHER INFORMATION: EPC100 HVR1

<400> SEQUENCE: 17
gaagcagatt tgggtaccac ccaagtattg actcacccat caacaaccgc tatgtatttc    60
gtacattact gccagccacc atgaatattg tacggtacca taaatacttg accacctgta    120
gtacataaaa acccaatcca catcaaaacc ccctcccat gcttacaagc aagtacagca    180
atcaaccttc aactatcaca catcaactgc aactccaaag ccaccctca cccactagg    239

<210> SEQ ID NO 18
<211> LENGTH: 15
<212> TYPE: DNA
<213> ORGANISM: Artificial Sequence
<220> FEATURE:
<223> OTHER INFORMATION: hTcell-probe - FAM

<400> SEQUENCE: 18
caaccaaccc tcaac    15

<210> SEQ ID NO 19
<211> LENGTH: 17
<212> TYPE: DNA
<213> ORGANISM: Artificial Sequence
<220> FEATURE:
<223> OTHER INFORMATION: EPC100-probe - VIC

<400> SEQUENCE: 19
agcaatcaac cttcaac    17

<210> SEQ ID NO 20
<211> LENGTH: 22

```
<212> TYPE: DNA
<213> ORGANISM: Artificial Sequence
<220> FEATURE:
<223> OTHER INFORMATION: HVR1-F-primer

<400> SEQUENCE: 20
ccccatgctt acaagcaagt ac                                              22

<210> SEQ ID NO 21
<211> LENGTH: 22
<212> TYPE: DNA
<213> ORGANISM: Artificial Sequence
<220> FEATURE:
<223> OTHER INFORMATION: HVR1-R-primer

<400> SEQUENCE: 21
ttggagttgc agttgatgtg tg                                              22

<210> SEQ ID NO 22
<211> LENGTH: 22
<212> TYPE: DNA
<213> ORGANISM: Artificial Sequence
<220> FEATURE:
<223> OTHER INFORMATION: hmtD_loop-F

<400> SEQUENCE: 22
ctctgttctt tcatggggaa gc                                              22

<210> SEQ ID NO 23
<211> LENGTH: 21
<212> TYPE: DNA
<213> ORGANISM: Artificial Sequence
<220> FEATURE:
<223> OTHER INFORMATION: EPC100 16362 A>G

<400> SEQUENCE: 23
atccatgggg acgagaaggg a                                               21

<210> SEQ ID NO 24
<211> LENGTH: 400
<212> TYPE: DNA
<213> ORGANISM: Artificial Sequence
<220> FEATURE:
<223> OTHER INFORMATION: EPC100 HVR1 with flacking sequences

<400> SEQUENCE: 24
attctaattt aaactattct ctgttctttc atggggaagc agatttgggt accacccaag     60
tattgactca cccatcaaca accgctatgt atttcgtaca ttactgccag ccaccatgaa    120
tattgtacgg taccataaat acttgaccac ctgtagtaca taaaaaccca atccacatca    180 aaccccctc cccatgctta caagcaagta cagcaatcaa ccctcaacta tcacacatca    240
actgcaactc caaagccacc cctcacccac taggatacca acaaacctac ccacccttaa    300
cagtacatag tacataaagc catttaccgt acatagcaca ttacagtcaa atcccttctc    360
gtccccatgg atgacccccc tcagataggg gtcccttgac                          400
```